(12) United States Patent
Seme et al.

(10) Patent No.: US 8,920,472 B2
(45) Date of Patent: Dec. 30, 2014

(54) SPINAL CORRECTION AND SECONDARY STABILIZATION

(71) Applicant: Kspine, Inc., Minnetonka, MN (US)

(72) Inventors: Steven J. Seme, Savage, MN (US); John F. Otte, Minneapolis, MN (US); Thomas J. Gisel, Chaska, MN (US)

(73) Assignee: Kspine, Inc., Minnetonka, MN (US)

( * ) Notice: Subject to any disclaimer, the term of this patent is extended or adjusted under 35 U.S.C. 154(b) by 0 days.

(21) Appl. No.: 13/865,775

(22) Filed: Apr. 18, 2013

(65) Prior Publication Data

US 2013/0231703 A1    Sep. 5, 2013

Related U.S. Application Data

(63) Continuation-in-part of application No. 13/297,841, filed on Nov. 16, 2011.

(51) Int. Cl.
    *A61B 17/70*      (2006.01)
    *A61B 17/88*      (2006.01)

(52) U.S. Cl.
    CPC ............ *A61B 17/88* (2013.01); *A61B 17/7049* (2013.01); *A61B 17/7052* (2013.01); *A61B 17/7019* (2013.01); *A61B 17/7004* (2013.01); *A61B 17/701* (2013.01); *A61B 17/704* (2013.01); *A61B 17/7041* (2013.01); *A61B 17/7044* (2013.01); *A61B 17/7053* (2013.01); *A61B 17/707* (2013.01)
    USPC .......................................... 606/251; 606/250

(58) Field of Classification Search
    USPC ................... 606/250–253, 256–257
    See application file for complete search history.

(56) References Cited

U.S. PATENT DOCUMENTS

| | | | |
|---|---|---|---|
| 2,774,350 A | 12/1956 | Cleveland, Jr. |
| 3,242,922 A | 3/1966 | Thomas |
| 3,352,226 A | 11/1967 | Nelsen |
| 3,648,691 A | 3/1972 | Lumb et al. |
| 3,693,616 A | 9/1972 | Roaf et al. |
| 3,865,105 A | 2/1975 | Lode |
| 4,024,588 A | 5/1977 | Janssen et al. |
| 4,078,559 A | 3/1978 | Nissinen |

(Continued)

FOREIGN PATENT DOCUMENTS

| | | |
|---|---|---|
| DE | 2644735 A1 | 4/1977 |
| DE | 2845647 A1 | 5/1980 |

(Continued)

OTHER PUBLICATIONS

Berry, James L. et al., A Morphometric Study of Human Lumbar and Selected Thoracic Vertebrae, 12 Spine 362 (1987).

(Continued)

*Primary Examiner* — Eduardo C. Robert
*Assistant Examiner* — Julianna N Harvey
(74) *Attorney, Agent, or Firm* — Faegre Baker Daniels LLP

(57) ABSTRACT

Methods of correcting a spinal deformity include securing a first rod on a first side of a spine, securing an anchor on a second side of a spine, securing a lateral coupling between the rod and the anchor, translating and derotating the spine to correct the spinal deformity by adjusting an effective length of the lateral coupling, and securing a second rod on a second side of the spine to provide secondary stabilization to the spine.

15 Claims, 14 Drawing Sheets

(56) References Cited

U.S. PATENT DOCUMENTS

| | | |
|---|---|---|
| 4,257,409 A | 3/1981 | Bacal et al. |
| 4,269,178 A | 5/1981 | Keene |
| 4,274,401 A | 6/1981 | Miskew |
| 4,355,645 A | 10/1982 | Mitani et al. |
| 4,361,141 A | 11/1982 | Tanner |
| 4,369,769 A | 1/1983 | Edwards |
| 4,404,967 A | 9/1983 | Bacal et al. |
| 4,411,259 A | 10/1983 | Drummond |
| 4,411,545 A | 10/1983 | Roberge |
| 4,448,191 A | 5/1984 | Rodnyansky et al. |
| 4,505,268 A | 3/1985 | Sgandurra |
| 4,554,914 A | 11/1985 | Kapp et al. |
| 4,573,454 A | 3/1986 | Hoffman |
| 4,604,995 A | 8/1986 | Stephens et al. |
| 4,611,581 A | 9/1986 | Steffee |
| 4,611,582 A | 9/1986 | Duff |
| 4,634,445 A | 1/1987 | Helal |
| 4,648,388 A | 3/1987 | Steffee |
| 4,653,481 A | 3/1987 | Howland et al. |
| 4,658,809 A | 4/1987 | Ulrich et al. |
| 4,697,582 A | 10/1987 | William |
| 4,738,251 A | 4/1988 | Plaza |
| 4,773,402 A | 9/1988 | Asher et al. |
| 4,805,602 A | 2/1989 | Puno et al. |
| 4,815,453 A | 3/1989 | Cotrel |
| 4,827,918 A | 5/1989 | Olerud |
| 4,854,311 A | 8/1989 | Steffee |
| 4,931,055 A | 6/1990 | Bumpus et al. |
| 4,936,848 A | 6/1990 | Bagby |
| 5,000,166 A | 3/1991 | Karpf |
| 5,005,562 A | 4/1991 | Cotrel |
| 5,011,484 A | 4/1991 | Breard |
| 5,030,220 A | 7/1991 | Howland |
| 5,042,982 A | 8/1991 | Harms et al. |
| 5,084,049 A | 1/1992 | Asher et al. |
| 5,092,866 A | 3/1992 | Breard et al. |
| 5,092,867 A | 3/1992 | Harms et al. |
| 5,127,912 A | 7/1992 | Ray et al. |
| 5,129,900 A | 7/1992 | Asher et al. |
| 5,133,716 A | 7/1992 | Plaza |
| 5,147,363 A | 9/1992 | Harle |
| 5,176,679 A | 1/1993 | Lin |
| 5,176,680 A | 1/1993 | Vignaud et al. |
| 5,181,917 A | 1/1993 | Rogozinski |
| 5,190,543 A | 3/1993 | Schlapfer |
| 5,196,014 A | 3/1993 | Lin |
| 5,207,678 A | 5/1993 | Harms et al. |
| 5,209,752 A | 5/1993 | Ashman et al. |
| 5,219,349 A | 6/1993 | Krag et al. |
| 5,242,443 A | 9/1993 | Kambin |
| 5,254,118 A | 10/1993 | Mirkovic |
| 5,257,994 A | 11/1993 | Lin |
| 5,259,398 A | 11/1993 | Vrespa |
| 5,282,862 A | 2/1994 | Baker et al. |
| 5,306,275 A | 4/1994 | Bryan |
| 5,312,404 A | 5/1994 | Asher et al. |
| 5,312,410 A | 5/1994 | Miller et al. |
| 5,312,420 A | 5/1994 | Toso et al. |
| 5,330,473 A | 7/1994 | Howland |
| 5,330,474 A | 7/1994 | Lin |
| 5,352,226 A | 10/1994 | Lin |
| 5,360,431 A | 11/1994 | Puno et al. |
| 5,366,455 A | 11/1994 | Dove et al. |
| 5,368,594 A | 11/1994 | Martin et al. |
| 5,380,323 A | 1/1995 | Howland |
| 5,380,325 A | 1/1995 | Lahille et al. |
| 5,382,248 A | 1/1995 | Jacobson et al. |
| 5,387,212 A | 2/1995 | Yuan et al. |
| 5,387,213 A | 2/1995 | Breard et al. |
| 5,391,168 A | 2/1995 | Sanders et al. |
| 5,397,363 A | 3/1995 | Gelbard |
| 5,413,576 A | 5/1995 | Rivard |
| 5,436,542 A | 7/1995 | Petelin et al. |
| 5,437,669 A | 8/1995 | Yuan et al. |
| 5,437,671 A | 8/1995 | Lozier et al. |
| 5,456,722 A | 10/1995 | McLeod et al. |
| 5,466,238 A | 11/1995 | Lin |
| 5,470,333 A | 11/1995 | Ray |
| 5,480,440 A | 1/1996 | Kambin |
| 5,486,174 A | 1/1996 | Fournet Fayard et al. |
| 5,487,744 A | 1/1996 | Howland |
| 5,490,851 A | 2/1996 | Nenov et al. |
| 5,496,318 A | 3/1996 | Howland et al. |
| 5,498,262 A | 3/1996 | Bryan |
| 5,501,684 A | 3/1996 | Schlapfer et al. |
| 5,520,688 A | 5/1996 | Lin |
| 5,527,314 A | 6/1996 | Brumfield et al. |
| 5,534,002 A | 7/1996 | Brumfield et al. |
| 5,540,689 A | 7/1996 | Sanders et al. |
| 5,544,993 A | 8/1996 | Harle |
| 5,549,679 A | 8/1996 | Kuslich |
| 5,562,660 A | 10/1996 | Grob |
| 5,562,662 A | 10/1996 | Brumfield et al. |
| 5,569,246 A | 10/1996 | Ojima et al. |
| 5,571,191 A | 11/1996 | Fitz |
| 5,575,791 A | 11/1996 | Lin |
| 5,584,626 A | 12/1996 | Assmundson |
| 5,586,983 A | 12/1996 | Sanders et al. |
| 5,591,165 A | 1/1997 | Jackson |
| 5,601,554 A | 2/1997 | Howland et al. |
| 5,609,592 A | 3/1997 | Brumfield et al. |
| 5,611,800 A | 3/1997 | Davis et al. |
| 5,620,443 A | 4/1997 | Gertzbein et al. |
| 5,630,816 A | 5/1997 | Kambin |
| 5,643,259 A | 7/1997 | Sasso et al. |
| 5,645,599 A | 7/1997 | Samani |
| 5,649,926 A | 7/1997 | Howland |
| 5,658,284 A | 8/1997 | Sebastian et al. |
| 5,672,175 A * | 9/1997 | Martin ........................ 606/86 A |
| 5,676,703 A | 10/1997 | Gelbard |
| 5,702,395 A | 12/1997 | Hopf |
| 5,702,399 A | 12/1997 | Kilpela et al. |
| 5,702,452 A | 12/1997 | Argenson et al. |
| 5,704,936 A | 1/1998 | Mazel |
| 5,713,898 A | 2/1998 | Stucker et al. |
| 5,716,355 A | 2/1998 | Jackson et al. |
| 5,725,582 A | 3/1998 | Bevan et al. |
| 5,728,097 A | 3/1998 | Mathews |
| 5,733,284 A | 3/1998 | Martin |
| 5,735,852 A | 4/1998 | Amrein et al. |
| 5,782,831 A | 7/1998 | Sherman et al. |
| 5,797,910 A | 8/1998 | Martin |
| 5,810,817 A | 9/1998 | Roussouly et al. |
| 5,810,819 A | 9/1998 | Errico et al. |
| 5,814,046 A | 9/1998 | Hopf |
| 5,885,285 A | 3/1999 | Simonson |
| 5,891,145 A | 4/1999 | Morrison et al. |
| 5,902,305 A | 5/1999 | Beger et al. |
| 5,910,142 A | 6/1999 | Tatar |
| 5,928,232 A | 7/1999 | Howland et al. |
| 5,938,663 A | 8/1999 | Petreto |
| 5,947,967 A | 9/1999 | Barker |
| 5,964,769 A | 10/1999 | Wagner et al. |
| 5,976,135 A | 11/1999 | Sherman et al. |
| 5,980,521 A | 11/1999 | Montague et al. |
| 5,984,924 A | 11/1999 | Asher et al. |
| 5,989,256 A | 11/1999 | Kuslich et al. |
| 6,015,409 A | 1/2000 | Jackson |
| 6,033,412 A | 3/2000 | Losken et al. |
| 6,039,738 A | 3/2000 | Sanders et al. |
| 6,053,921 A | 4/2000 | Wagner et al. |
| 6,066,140 A | 5/2000 | Gertzbein et al. |
| 6,077,268 A | 6/2000 | Farris et al. |
| 6,080,156 A | 6/2000 | Asher et al. |
| 6,083,224 A | 7/2000 | Gertzbein et al. |
| 6,086,590 A | 7/2000 | Margulies et al. |
| 6,101,678 A | 8/2000 | Malloy et al. |
| 6,110,173 A | 8/2000 | Thomas, Jr. |
| 6,123,706 A | 9/2000 | Lange |
| 6,132,431 A | 10/2000 | Nilsson et al. |
| 6,132,464 A | 10/2000 | Martin |
| 6,136,000 A | 10/2000 | Louis et al. |
| 6,176,861 B1 | 1/2001 | Bernstein et al. |
| 6,231,575 B1 | 5/2001 | Krag |

(56) References Cited

U.S. PATENT DOCUMENTS

| | | |
|---|---|---|
| 6,248,106 B1 | 6/2001 | Ferree |
| 6,251,111 B1 | 6/2001 | Barker et al. |
| 6,254,603 B1 | 7/2001 | Gertzbein et al. |
| 6,261,288 B1 | 7/2001 | Jackson |
| 6,273,914 B1 | 8/2001 | Papas |
| 6,277,120 B1 | 8/2001 | Lawson |
| 6,283,967 B1 | 9/2001 | Troxell et al. |
| 6,293,949 B1 | 9/2001 | Justis et al. |
| 6,296,643 B1 | 10/2001 | Hopf et al. |
| 6,299,613 B1 | 10/2001 | Ogilvie et al. |
| 6,325,805 B1 | 12/2001 | Ogilvie et al. |
| 6,328,739 B1 | 12/2001 | Liu et al. |
| 6,358,254 B1 | 3/2002 | Anderson |
| 6,364,883 B1 | 4/2002 | Santilli |
| 6,364,885 B1 | 4/2002 | Kilpela et al. |
| 6,391,030 B1 | 5/2002 | Wagner et al. |
| 6,402,749 B1 | 6/2002 | Ashman |
| 6,402,752 B2 | 6/2002 | Schäffler Wachter et al. |
| 6,419,703 B1 | 7/2002 | Fallin et al. |
| 6,423,065 B2 | 7/2002 | Ferree |
| 6,451,019 B1 | 9/2002 | Zucherman et al. |
| 6,458,131 B1 | 10/2002 | Ray |
| 6,471,704 B2 | 10/2002 | Gertzbein et al. |
| 6,488,683 B2 | 12/2002 | Lieberman |
| 6,514,255 B1 | 2/2003 | Ferree |
| 6,520,962 B1 | 2/2003 | Taylor et al. |
| 6,537,276 B2 | 3/2003 | Metz Stavenhagen |
| 6,547,789 B1 | 4/2003 | Ventre et al. |
| 6,551,320 B2 | 4/2003 | Lieberman |
| 6,554,831 B1 | 4/2003 | Rivard et al. |
| 6,562,038 B1 | 5/2003 | Morrison |
| 6,565,569 B1 | 5/2003 | Assaker et al. |
| 6,565,605 B2 | 5/2003 | Goble et al. |
| 6,569,164 B1 | 5/2003 | Assaker et al. |
| 6,579,292 B2 | 6/2003 | Taylor |
| 6,579,319 B2 | 6/2003 | Goble et al. |
| 6,582,433 B2 | 6/2003 | Yun |
| 6,585,738 B1 | 7/2003 | Mangione et al. |
| 6,589,243 B1 | 7/2003 | Viart et al. |
| 6,602,254 B2 | 8/2003 | Gertzbein et al. |
| 6,602,818 B2 | 8/2003 | Choi et al. |
| 6,610,091 B1 | 8/2003 | Reiley |
| 6,616,669 B2 | 9/2003 | Ogilvie et al. |
| 6,623,484 B2 | 9/2003 | Betz et al. |
| 6,626,906 B1 | 9/2003 | Young |
| 6,626,909 B2 | 9/2003 | Chin |
| 6,641,585 B2 | 11/2003 | Sato et al. |
| 6,645,207 B2 | 11/2003 | Dixon et al. |
| 6,651,320 B1 | 11/2003 | Yagi et al. |
| 6,656,185 B2 | 12/2003 | Gleason et al. |
| 6,669,729 B2 | 12/2003 | Chin |
| 6,682,532 B2 | 1/2004 | Johnson et al. |
| 6,682,533 B1 | 1/2004 | Dinsdale et al. |
| 6,685,705 B1 | 2/2004 | Taylor |
| 6,689,133 B2 | 2/2004 | Morrison et al. |
| 6,709,435 B2 | 3/2004 | Lin |
| 6,736,817 B2 | 5/2004 | Troxell et al. |
| 6,749,612 B1 | 6/2004 | Conchy et al. |
| 6,755,828 B2 | 6/2004 | Shevtsov et al. |
| 6,773,437 B2 | 8/2004 | Ogilvie et al. |
| 6,802,844 B2 | 10/2004 | Ferree |
| 6,811,567 B2 | 11/2004 | Reiley |
| 6,835,207 B2 | 12/2004 | Zacouto et al. |
| 6,840,127 B2 | 1/2005 | Moran |
| 6,860,884 B2 | 3/2005 | Shirado et al. |
| 6,887,241 B1 | 5/2005 | McBride et al. |
| 6,902,580 B2 | 6/2005 | Fallin et al. |
| 6,946,000 B2 | 9/2005 | Senegas et al. |
| 6,966,910 B2 | 11/2005 | Ritland |
| 6,966,930 B2 | 11/2005 | Arnin et al. |
| 6,974,478 B2 | 12/2005 | Reiley et al. |
| 6,986,771 B2 | 1/2006 | Paul et al. |
| 7,008,423 B2 | 3/2006 | Assaker et al. |
| 7,018,379 B2 | 3/2006 | Drewry et al. |
| 7,029,475 B2 | 4/2006 | Panjabi |
| 7,041,136 B2 | 5/2006 | Goble et al. |
| 7,048,736 B2 | 5/2006 | Robinson et al. |
| 7,051,451 B2 | 5/2006 | Augostino et al. |
| 7,074,237 B2 | 7/2006 | Goble et al. |
| 7,083,621 B2 | 8/2006 | Shaolian et al. |
| 7,087,056 B2 | 8/2006 | Vaughan |
| 7,090,698 B2 | 8/2006 | Goble et al. |
| 7,104,992 B2 | 9/2006 | Bailey |
| RE39,325 E | 10/2006 | Bryan |
| 7,128,743 B2 | 10/2006 | Metz Stavenhagen |
| 7,137,986 B2 | 11/2006 | Troxell et al. |
| 7,160,312 B2 | 1/2007 | Saadat |
| 7,220,262 B1 | 5/2007 | Hynes |
| 7,261,714 B2 | 8/2007 | Richelsoph |
| 7,270,665 B2 | 9/2007 | Morrison et al. |
| 7,290,347 B2 | 11/2007 | Augostino et al. |
| 7,294,129 B2 | 11/2007 | Hawkins et al. |
| 7,316,684 B1 | 1/2008 | Baccelli et al. |
| 7,335,203 B2 | 2/2008 | Winslow et al. |
| 7,338,490 B2 | 3/2008 | Ogilvie et al. |
| 7,344,539 B2 | 3/2008 | Serhan et al. |
| 7,361,196 B2 | 4/2008 | Fallin et al. |
| 7,367,978 B2 | 5/2008 | Drewry et al. |
| 7,406,775 B2 | 8/2008 | Funk et al. |
| 7,445,635 B2 | 11/2008 | Fallin et al. |
| 7,473,267 B2 | 1/2009 | Nguyen et al. |
| 7,473,269 B1 | 1/2009 | Hynes |
| 7,481,828 B2 | 1/2009 | Mazda et al. |
| 7,507,242 B2 | 3/2009 | Triplett et al. |
| 7,524,324 B2 | 4/2009 | Winslow et al. |
| 7,566,345 B1 | 7/2009 | Fallin et al. |
| 7,588,578 B2 | 9/2009 | Triplett et al. |
| 7,588,590 B2 | 9/2009 | Chervitz et al. |
| 7,591,836 B2 | 9/2009 | Dick et al. |
| 7,594,924 B2 | 9/2009 | Albert et al. |
| 7,611,526 B2 | 11/2009 | Carl et al. |
| 7,618,453 B2 | 11/2009 | Goble et al. |
| 7,618,455 B2 | 11/2009 | Goble et al. |
| 7,621,955 B2 | 11/2009 | Goble et al. |
| 7,648,521 B2 | 1/2010 | Hestad |
| 7,658,753 B2 | 2/2010 | Carl et al. |
| 7,674,293 B2 | 3/2010 | Kuiper et al. |
| 7,678,136 B2 | 3/2010 | Doubler et al. |
| 7,691,145 B2 | 4/2010 | Reiley et al. |
| 7,708,762 B2 | 5/2010 | McCarthy et al. |
| 7,717,940 B2 | 5/2010 | Woods et al. |
| 7,717,942 B2 | 5/2010 | Schumacher |
| 7,722,647 B1 | 5/2010 | Wang et al. |
| 7,722,648 B2 | 5/2010 | Drewry et al. |
| 7,753,937 B2 | 7/2010 | Chervitz et al. |
| 7,758,581 B2 | 7/2010 | Chervitz et al. |
| 7,771,474 B2 | 8/2010 | Cordaro |
| 7,794,476 B2 | 9/2010 | Wisnewski |
| 7,794,478 B2 | 9/2010 | Nilsson |
| 7,799,054 B2 | 9/2010 | Kwak et al. |
| 7,819,902 B2 | 10/2010 | Abdelgany et al. |
| 7,833,252 B2 | 11/2010 | Justis et al. |
| 7,837,714 B2 | 11/2010 | Drewry et al. |
| 7,842,071 B2 | 11/2010 | Hawkes |
| 7,862,586 B2 | 1/2011 | Malek |
| 7,896,906 B2 | 3/2011 | Kwak et al. |
| 7,918,876 B2 | 4/2011 | Mueller et al. |
| 7,927,359 B2 | 4/2011 | Trautwein et al. |
| 7,931,676 B2 | 4/2011 | Veldman et al. |
| 7,935,134 B2 | 5/2011 | Reglos et al. |
| 7,942,902 B2 | 5/2011 | Schwab |
| 7,959,653 B2 | 6/2011 | Thramann et al. |
| 7,963,978 B2 | 6/2011 | Winslow et al. |
| 7,985,243 B2 | 7/2011 | Winslow et al. |
| 8,012,184 B2 | 9/2011 | Schlapfer et al. |
| 8,016,860 B2 | 9/2011 | Carl et al. |
| 8,021,400 B2 | 9/2011 | Marino et al. |
| 8,029,543 B2 | 10/2011 | Young et al. |
| 8,029,546 B2 | 10/2011 | Capote et al. |
| 8,034,078 B2 | 10/2011 | Laskowitz et al. |
| 8,034,084 B2 | 10/2011 | Landry et al. |
| 8,043,345 B2 | 10/2011 | Carl et al. |
| 8,048,113 B2 | 11/2011 | Winslow et al. |
| 8,052,722 B2 | 11/2011 | Winslow et al. |

(56) References Cited

U.S. PATENT DOCUMENTS

| | | |
|---|---|---|
| 8,066,743 B2 | 11/2011 | Young et al. |
| 8,070,775 B2 | 12/2011 | Winslow et al. |
| 8,070,776 B2 | 12/2011 | Winslow et al. |
| 8,075,594 B2 | 12/2011 | Purcell |
| 8,097,022 B2 | 1/2012 | Marik |
| 8,114,134 B2 | 2/2012 | Winslow et al. |
| 8,114,158 B2 | 2/2012 | Carl et al. |
| 8,118,837 B2 | 2/2012 | Lemoine |
| 8,147,524 B2 | 4/2012 | Piza Vallespir |
| 8,162,979 B2 | 4/2012 | Sachs et al. |
| 8,167,908 B2 | 5/2012 | Ely et al. |
| 8,192,471 B2 | 6/2012 | Ludwig et al. |
| 8,221,466 B2 | 7/2012 | Asaad et al. |
| 8,262,696 B2 | 9/2012 | Falahee |
| 8,292,934 B2 | 10/2012 | Justis et al. |
| 8,323,319 B2 | 12/2012 | Mazda et al. |
| 8,353,934 B2 | 1/2013 | Drewry et al. |
| 8,357,182 B2 | 1/2013 | Seme |
| 8,357,183 B2 | 1/2013 | Seme et al. |
| 8,361,117 B2 | 1/2013 | Michielli et al. |
| 8,403,958 B2 | 3/2013 | Schwab |
| 8,414,614 B2 | 4/2013 | Firkins et al. |
| 8,414,617 B2 | 4/2013 | Young et al. |
| 8,470,001 B2 | 6/2013 | Trautwein et al. |
| RE44,392 E | 7/2013 | Hynes |
| 8,475,499 B2 | 7/2013 | Cournoyer et al. |
| 8,480,712 B1 | 7/2013 | Samuel et al. |
| 8,518,086 B2 | 8/2013 | Seme et al. |
| 2001/0037111 A1 | 11/2001 | Dixon et al. |
| 2002/0032442 A1 | 3/2002 | Altarac et al. |
| 2002/0133155 A1 | 9/2002 | Ferree |
| 2002/0143329 A1 | 10/2002 | Serhan et al. |
| 2002/0151978 A1 | 10/2002 | Zacouto et al. |
| 2003/0040746 A1 | 2/2003 | Mitchell et al. |
| 2003/0045878 A1 | 3/2003 | Petit et al. |
| 2003/0093117 A1 | 5/2003 | Saadat |
| 2003/0109881 A1 | 6/2003 | Shirado et al. |
| 2003/0114853 A1 | 6/2003 | Burgess et al. |
| 2003/0153915 A1 | 8/2003 | Nekozuka et al. |
| 2003/0220643 A1 | 11/2003 | Ferree |
| 2004/0006391 A1 | 1/2004 | Reiley |
| 2004/0049274 A1 | 3/2004 | Reiley |
| 2004/0049277 A1 | 3/2004 | Reiley |
| 2004/0097931 A1 | 5/2004 | Mitchell |
| 2004/0106921 A1 | 6/2004 | Cheung et al. |
| 2004/0149065 A1 | 8/2004 | Moran |
| 2004/0167520 A1 | 8/2004 | Zucherman et al. |
| 2004/0215190 A1 | 10/2004 | Nguyen et al. |
| 2004/0230201 A1 | 11/2004 | Yuan et al. |
| 2004/0230304 A1 | 11/2004 | Yuan et al. |
| 2005/0027361 A1 | 2/2005 | Reiley |
| 2005/0033291 A1 | 2/2005 | Ebara |
| 2005/0033295 A1 | 2/2005 | Wisnewski |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0080420 A1 | 4/2005 | Farris et al. |
| 2005/0080486 A1 | 4/2005 | Fallin et al. |
| 2005/0107789 A1 | 5/2005 | Sweeney |
| 2005/0113927 A1 | 5/2005 | Malek |
| 2005/0113928 A1 | 5/2005 | Cragg et al. |
| 2005/0131537 A1 | 6/2005 | Hoy et al. |
| 2005/0131538 A1 | 6/2005 | Chervitz et al. |
| 2005/0149030 A1 | 7/2005 | Serhan et al. |
| 2005/0154390 A1 | 7/2005 | Biedermann et al. |
| 2005/0165396 A1 | 7/2005 | Fortin et al. |
| 2005/0171538 A1 | 8/2005 | Sgier et al. |
| 2005/0177240 A1 | 8/2005 | Blain |
| 2005/0203509 A1 | 9/2005 | Chinnaian et al. |
| 2005/0203511 A1 | 9/2005 | Wilson MacDonald et al. |
| 2005/0203514 A1 | 9/2005 | Jahng et al. |
| 2005/0203516 A1 | 9/2005 | Biedermann et al. |
| 2005/0209603 A1 | 9/2005 | Zucherman et al. |
| 2005/0216004 A1 | 9/2005 | Schwab |
| 2005/0228326 A1 | 10/2005 | Kalfas et al. |
| 2005/0228377 A1 | 10/2005 | Chao et al. |
| 2005/0234453 A1 | 10/2005 | Shaolian et al. |
| 2005/0240264 A1 | 10/2005 | Tokish et al. |
| 2005/0245929 A1 | 11/2005 | Winslow et al. |
| 2005/0261685 A1 | 11/2005 | Fortin et al. |
| 2005/0261770 A1 | 11/2005 | Kuiper et al. |
| 2005/0267470 A1 | 12/2005 | McBride |
| 2005/0267579 A1 | 12/2005 | Reiley et al. |
| 2006/0004449 A1 | 1/2006 | Goble et al. |
| 2006/0009767 A1 | 1/2006 | Kiester |
| 2006/0009847 A1 | 1/2006 | Reiley |
| 2006/0009849 A1 | 1/2006 | Reiley |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058790 A1 | 3/2006 | Carl et al. |
| 2006/0058791 A1 | 3/2006 | Broman et al. |
| 2006/0058792 A1 | 3/2006 | Hynes |
| 2006/0064091 A1 | 3/2006 | Ludwig et al. |
| 2006/0084976 A1 | 4/2006 | Borgstrom et al. |
| 2006/0084996 A1 | 4/2006 | Metz Stavenhagen |
| 2006/0085075 A1 | 4/2006 | McLeer |
| 2006/0116686 A1 | 6/2006 | Crozet |
| 2006/0142758 A1 | 6/2006 | Petit |
| 2006/0142760 A1 | 6/2006 | McDonnell |
| 2006/0149234 A1 | 7/2006 | de Coninck |
| 2006/0189984 A1 | 8/2006 | Fallin et al. |
| 2006/0200149 A1 | 9/2006 | Hoy et al. |
| 2006/0212034 A1 | 9/2006 | Triplett et al. |
| 2006/0217712 A1 | 9/2006 | Mueller et al. |
| 2006/0217715 A1 | 9/2006 | Serhan et al. |
| 2006/0217718 A1 | 9/2006 | Chervitz et al. |
| 2006/0229616 A1 | 10/2006 | Albert et al. |
| 2006/0241594 A1 | 10/2006 | McCarthy et al. |
| 2006/0241598 A1 | 10/2006 | Khalili |
| 2006/0247627 A1 | 11/2006 | Farris |
| 2006/0253118 A1 | 11/2006 | Bailey |
| 2006/0271050 A1 | 11/2006 | Piza Vallespir |
| 2006/0276787 A1 | 12/2006 | Zubok et al. |
| 2006/0293663 A1 | 12/2006 | Walkenhorst et al. |
| 2007/0005062 A1 | 1/2007 | Lange et al. |
| 2007/0016296 A1 | 1/2007 | Triplett et al. |
| 2007/0055373 A1 | 3/2007 | Hudgins et al. |
| 2007/0073293 A1 | 3/2007 | Martz et al. |
| 2007/0079517 A1 | 4/2007 | Augostino et al. |
| 2007/0083200 A1 | 4/2007 | Gittings et al. |
| 2007/0093814 A1 | 4/2007 | Callahan et al. |
| 2007/0093833 A1 | 4/2007 | Kuiper et al. |
| 2007/0161987 A1 | 7/2007 | Capote et al. |
| 2007/0161994 A1 | 7/2007 | Lowery et al. |
| 2007/0162002 A1 | 7/2007 | Tornier |
| 2007/0167946 A1 | 7/2007 | Triplett et al. |
| 2007/0167947 A1 | 7/2007 | Gittings |
| 2007/0168035 A1 | 7/2007 | Koske |
| 2007/0185492 A1 | 8/2007 | Chervitz et al. |
| 2007/0191846 A1 | 8/2007 | Bruneau et al. |
| 2007/0198014 A1 | 8/2007 | Graf et al. |
| 2007/0213716 A1 | 9/2007 | Lenke et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0233075 A1 | 10/2007 | Dawson |
| 2007/0233090 A1 | 10/2007 | Naifeh et al. |
| 2007/0233093 A1 | 10/2007 | Falahee |
| 2007/0238335 A1 | 10/2007 | Veldman et al. |
| 2007/0270803 A1 | 11/2007 | Giger et al. |
| 2007/0270805 A1 | 11/2007 | Miller et al. |
| 2007/0270817 A1 | 11/2007 | Rezach |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0270967 A1 | 11/2007 | Fallin et al. |
| 2007/0276374 A1 | 11/2007 | Broman et al. |
| 2007/0288011 A1 | 12/2007 | Logan |
| 2007/0288024 A1 | 12/2007 | Gollogly |

(56) References Cited

U.S. PATENT DOCUMENTS

| | | |
|---|---|---|
| 2008/0015577 A1 | 1/2008 | Loeb |
| 2008/0021466 A1 | 1/2008 | Shadduck et al. |
| 2008/0021469 A1 | 1/2008 | Holt |
| 2008/0027436 A1 | 1/2008 | Cournoyer et al. |
| 2008/0045954 A1 | 2/2008 | Reiley et al. |
| 2008/0065069 A1 | 3/2008 | Betz et al. |
| 2008/0077143 A1 | 3/2008 | Shluzas |
| 2008/0086213 A1 | 4/2008 | Reiley |
| 2008/0091202 A1 | 4/2008 | Reiley |
| 2008/0091210 A1 | 4/2008 | Reiley |
| 2008/0091268 A1 | 4/2008 | Reiley |
| 2008/0097437 A1 | 4/2008 | Reiley |
| 2008/0097438 A1 | 4/2008 | Reiley |
| 2008/0097439 A1 | 4/2008 | Reiley |
| 2008/0097440 A1 | 4/2008 | Reiley et al. |
| 2008/0097441 A1 | 4/2008 | Hayes et al. |
| 2008/0097446 A1 | 4/2008 | Reiley et al. |
| 2008/0097609 A1 | 4/2008 | Reiley |
| 2008/0097612 A1 | 4/2008 | Reiley |
| 2008/0097613 A1 | 4/2008 | Reiley et al. |
| 2008/0132951 A1 | 6/2008 | Reiley et al. |
| 2008/0140202 A1 | 6/2008 | Allard et al. |
| 2008/0167688 A1 | 7/2008 | Fauth et al. |
| 2008/0177326 A1 | 7/2008 | Thompson |
| 2008/0183209 A1 | 7/2008 | Robinson et al. |
| 2008/0183212 A1 | 7/2008 | Veldman et al. |
| 2008/0195100 A1 | 8/2008 | Capote et al. |
| 2008/0195153 A1 | 8/2008 | Thompson |
| 2008/0195154 A1 | 8/2008 | Brown et al. |
| 2008/0200953 A1 | 8/2008 | Reiley et al. |
| 2008/0221622 A1 | 9/2008 | Triplett et al. |
| 2008/0228227 A1 | 9/2008 | Brown et al. |
| 2008/0234737 A1 | 9/2008 | Boschert |
| 2008/0234739 A1 | 9/2008 | Hudgins et al. |
| 2008/0262546 A1 | 10/2008 | Calvosa et al. |
| 2008/0269805 A1 | 10/2008 | Dekutoski et al. |
| 2008/0275507 A1 | 11/2008 | Triplett et al. |
| 2008/0292161 A1 | 11/2008 | Funk et al. |
| 2008/0306535 A1 | 12/2008 | Winslow et al. |
| 2008/0306536 A1 | 12/2008 | Frigg et al. |
| 2008/0319483 A1 | 12/2008 | Triplett et al. |
| 2008/0319484 A1 | 12/2008 | Fauth |
| 2008/0319485 A1 | 12/2008 | Fauth et al. |
| 2008/0319488 A1 | 12/2008 | Helgerson |
| 2008/0319489 A1 | 12/2008 | Triplett |
| 2009/0012565 A1 | 1/2009 | Sachs et al. |
| 2009/0012566 A1 | 1/2009 | Fauth |
| 2009/0018583 A1 | 1/2009 | Song et al. |
| 2009/0024134 A1 | 1/2009 | Triplett et al. |
| 2009/0024135 A1 | 1/2009 | Triplett et al. |
| 2009/0024166 A1 | 1/2009 | Carl et al. |
| 2009/0024167 A1 | 1/2009 | Chervitz et al. |
| 2009/0024168 A1 | 1/2009 | Chervitz et al. |
| 2009/0024169 A1 | 1/2009 | Triplett et al. |
| 2009/0030459 A1 | 1/2009 | Hoy et al. |
| 2009/0030460 A1 | 1/2009 | Chervitz et al. |
| 2009/0030461 A1 | 1/2009 | Hoy et al. |
| 2009/0036929 A1 | 2/2009 | Reglos et al. |
| 2009/0048632 A1 | 2/2009 | Firkins et al. |
| 2009/0062864 A1 | 3/2009 | Ludwig et al. |
| 2009/0062915 A1 | 3/2009 | Kohm et al. |
| 2009/0069849 A1 | 3/2009 | Oh et al. |
| 2009/0082871 A1 | 3/2009 | Fallin et al. |
| 2009/0088802 A1 | 4/2009 | Fallin |
| 2009/0093820 A1 | 4/2009 | Trieu et al. |
| 2009/0099607 A1 | 4/2009 | Fallin et al. |
| 2009/0112207 A1 | 4/2009 | Walker et al. |
| 2009/0112262 A1 | 4/2009 | Pool et al. |
| 2009/0112263 A1 | 4/2009 | Pool et al. |
| 2009/0125062 A1 | 5/2009 | Arnin |
| 2009/0194206 A1 | 8/2009 | Jeon et al. |
| 2009/0204156 A1 | 8/2009 | McClintock et al. |
| 2009/0259256 A1 | 10/2009 | Miller |
| 2009/0281575 A1 | 11/2009 | Carls et al. |
| 2010/0057129 A1 | 3/2010 | Goble et al. |
| 2010/0076493 A1 | 3/2010 | Fauth et al. |
| 2010/0082107 A1 | 4/2010 | Fauth et al. |
| 2010/0087880 A1 | 4/2010 | Fauth et al. |
| 2010/0100130 A1 | 4/2010 | Carl et al. |
| 2010/0100133 A1 | 4/2010 | Carl et al. |
| 2010/0106192 A1 | 4/2010 | Barry |
| 2010/0137913 A1 | 6/2010 | Khatchadourian et al. |
| 2010/0249836 A1 | 9/2010 | Seme |
| 2010/0249837 A1 | 9/2010 | Seme et al. |
| 2010/0256684 A1 | 10/2010 | Seme et al. |
| 2010/0274286 A1 | 10/2010 | Blain et al. |
| 2010/0286730 A1 | 11/2010 | Gordon |
| 2010/0318129 A1 | 12/2010 | Seme et al. |
| 2011/0054536 A1 | 3/2011 | Elsebaie et al. |
| 2011/0060367 A1 | 3/2011 | Stauber |
| 2011/0066188 A1 | 3/2011 | Seme et al. |
| 2011/0245876 A1 | 10/2011 | Brumfield |
| 2012/0109197 A1 | 5/2012 | Carl et al. |
| 2012/0221057 A1 | 8/2012 | Zhang et al. |
| 2013/0123851 A1 | 5/2013 | Seme et al. |
| 2013/0123853 A1 | 5/2013 | Seme et al. |
| 2013/0184757 A1 | 7/2013 | Seme et al. |
| 2013/0211455 A1 | 8/2013 | Seme |

FOREIGN PATENT DOCUMENTS

| | | |
|---|---|---|
| EP | 0418387 A1 | 3/1991 |
| EP | 0260044 B1 | 5/1991 |
| EP | 0322334 B1 | 2/1992 |
| EP | 1281361 A1 | 2/2003 |
| FR | 2697744 A1 | 5/1994 |
| FR | 2736535 A1 | 1/1997 |
| FR | 2781359 A1 | 1/2000 |
| FR | 2801492 A1 | 6/2001 |
| FR | 2872021 A1 | 12/2005 |
| FR | 2900563 A1 | 11/2007 |
| GB | 0780652 A | 8/1957 |
| SU | 0888968 A1 | 12/1981 |
| WO | WO9213496 A1 | 8/1992 |
| WO | WO2004007705 A2 | 3/2004 |
| WO | WO2006010844 A1 | 2/2006 |
| WO | WO2006017641 A2 | 2/2006 |
| WO | WO2006136937 A2 | 12/2006 |
| WO | WO2007051924 A1 | 5/2007 |
| WO | WO2008086467 A2 | 7/2008 |
| WO | WO2008154313 A1 | 12/2008 |
| WO | WO2010053662 A1 | 5/2010 |
| WO | WO2010056650 A1 | 5/2010 |
| WO | WO2010111500 A2 | 9/2010 |

OTHER PUBLICATIONS

European Search Report issued in EP Application No. 12154799, completed Mar. 2, 2012, 9 pages.

Fujita, Masaru et al., A Biomechanical Analysis of Sublaminar and Subtransverse Process Fixation Using Metal Wires and Polyethylene Cables, 31 Spine 2202 (2006).

Girardi, Federico P. et al., Safety of Sublaminar Wires With Isola Instrumentation for the Treatment of Idiopathic Scoliosis, 25 Spine 691 (2000).

International Application No. PCT/US2008/065979, filed Jun. 5, 2008, entitled Medical Device and Method to Correct Deformity.

International Application No. PCT/US2009/063833, filed Nov. 10, 2009, entitled Growth Directed Vertebral Fixation System With Distractible Connector(s) and Apical Control.

International Application No. PCT/US2010/028684, filed Mar. 25, 2010, entitled Semi-Constrained Anchoring System.

International Search Report and Written Opinion issued in PCT/US2005/027692, mailed May 19, 2008, 4 pages.

International Search Report and Written Opinion issued in PCT/US2008/065979, mailed Oct. 2, 2008, 7 pages.

International Search Report and Written Opinion issued in PCT/US2009/063833, mailed Mar. 15, 2010, 14 pages.

International Search Report and Written Opinion issued in PCT/US2010/028684, mailed Sep. 28, 2010, 19 pages.

International Search Report and Written Opinion issued in PCT/US2010/036375, mailed Sep. 10, 2010, 16 pages.

(56) References Cited

OTHER PUBLICATIONS

International Search Report and Written Opinion issued in PCT/US2010/047117, mailed Dec. 2, 2010.
International Search Report and Written Opinion issued in PCT/US2011/049693, mailed Nov. 15, 2011, 16 pages.
International Search Report and Written Opinion issued in PCT/US2012/065262, mailed Feb. 5, 2013, 8 pages.
Invitation to Pay Additional Fees and Partial Search Report issued in PCT/US2010/028684, mailed Jun. 30, 2010, 6 pages.
Liljenqvist, Ulf R. et al., Analysis of Vertebral Morphology in Idiopathic Scoliosis with Use of Magnetic Resonance Imaging and Multiplanar Reconstruction, 84 J Bone Joint Surg Am. 359 (2002).
Molnar, Szabolcs et al., Ex Vivo and In Vitro Determination of the Axial Rotational Axis of the Human Thoracic Spine, 31 Spine E984 (2006).
Rajasekaran, S. et al., Eighteen-Level Analysis of Vertebral Rotation Following Harrington-Luque Instrumentation in Idiopathic Scoliosis, 76 J Bone Joint Surg Am. 104 (1994).
U.S. Appl. No. 12/411,558, filed Mar. 26, 2009, entitled Alignment System With Longitudinal Support Features.
U.S. Appl. No. 12/411,562, filed Mar. 26, 2009, entitled Semi-Constrained Anchoring System.
U.S. Appl. No. 12/485,796, filed Jun. 16, 2009 entitled Deformity Alignment System With Reactive Force Balancing.
U.S. Appl. No. 12/560,199, filed Sep. 15, 2009, entitled Growth Modulation System.
Wenger, Dennis R. et al., Biomechanics of Scoliosis Correction by Segmental Spinal Instrumentation, 7 Spine 260 (1982).
White III, Augustus A. et al., Biomechancis of the Spine 28-29, Tbl. 1-5 (2d ed. 1990).
International Search Report and Written Opinion issued in PCT/US2012/040493, mailed Aug. 21, 2012, 15 pages.
International Search Report and Written Opinion issued in PCT/US2013/065488, mailed Feb. 18, 2014, 10 pages.

\* cited by examiner

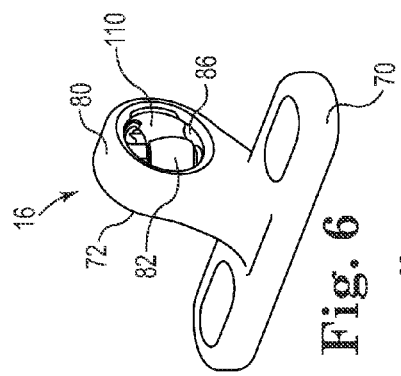
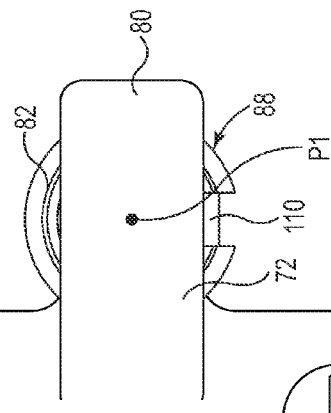
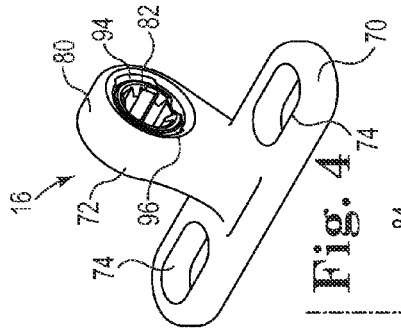
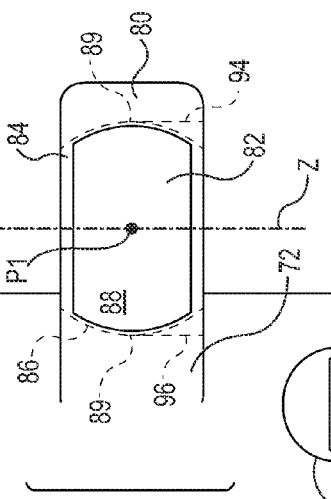

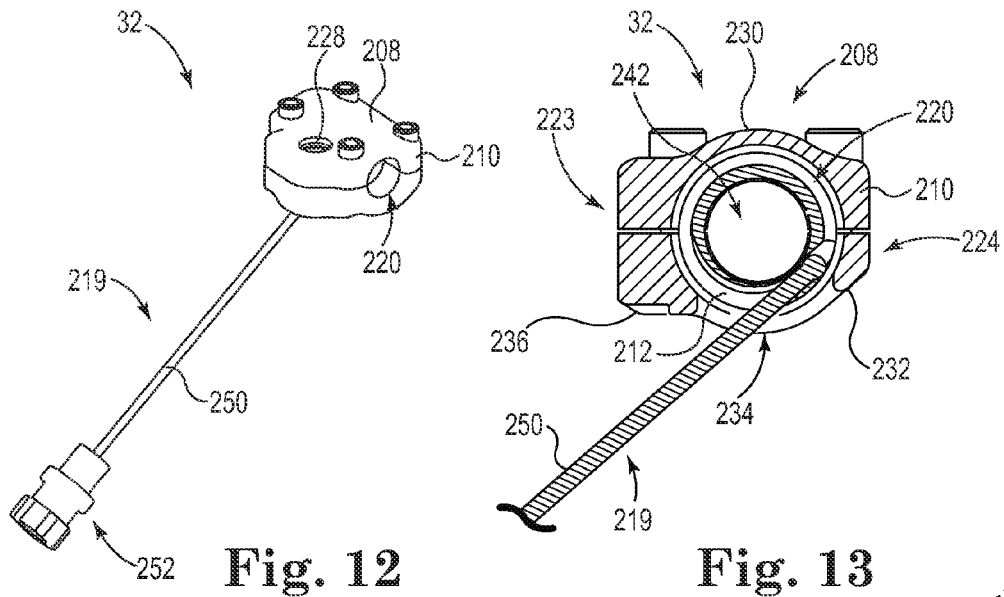
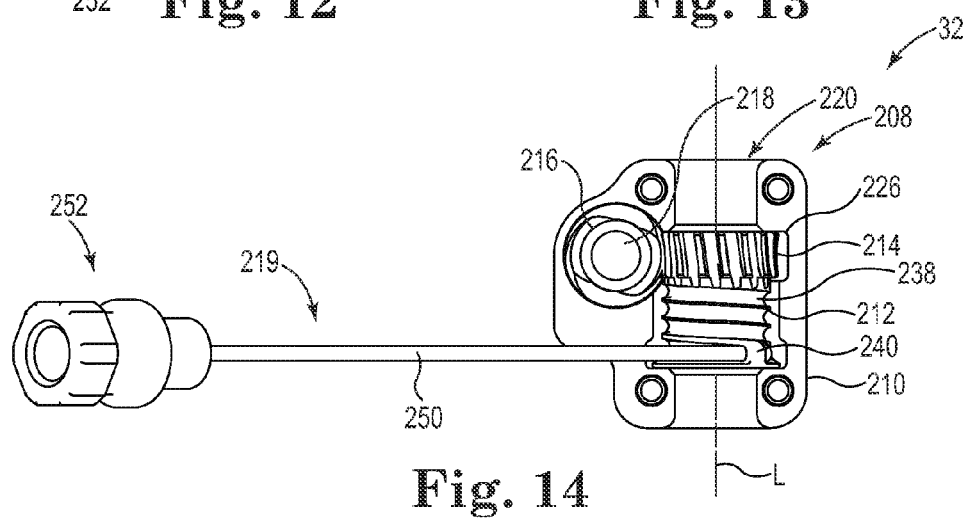
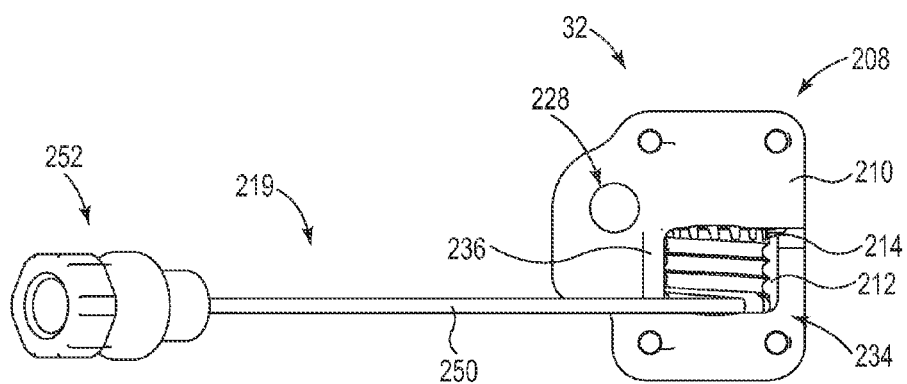

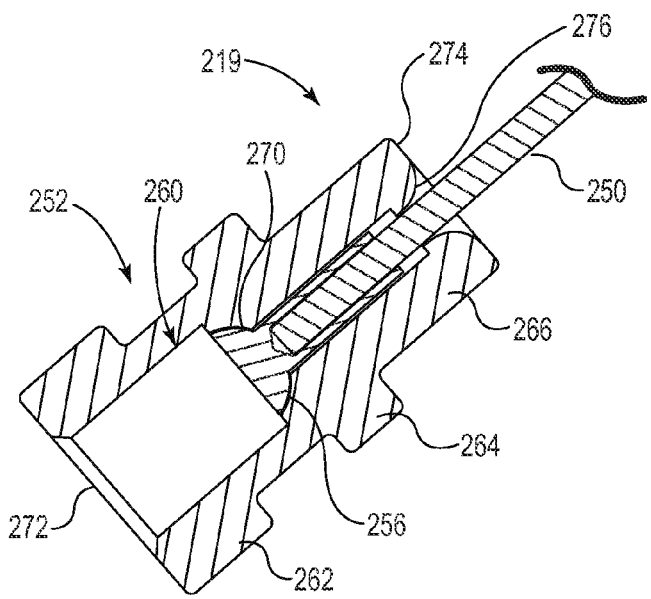
Fig. 16
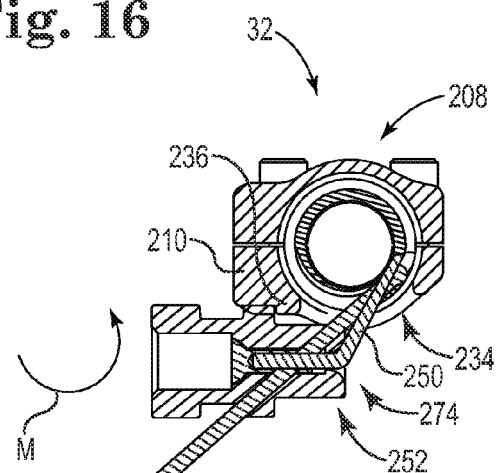
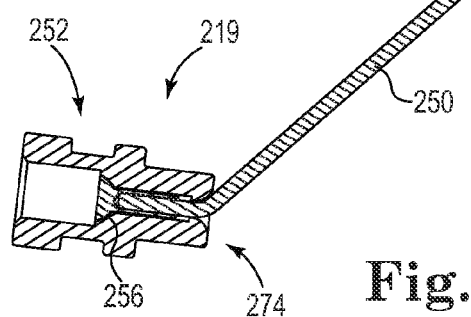
Fig. 17

SPINAL CORRECTION AND SECONDARY STABILIZATION

CROSS-REFERENCE TO RELATED APPLICATIONS

This application claims priority under 35 U.S.C. 120 to, and is a continuation-in-part of U.S. application Ser. No. 13/297,841, filed Nov. 16, 2011, and titled, "Spinal Correction and Secondary Stabilization," the entire contents of which are incorporated herein by reference.

INCORPORATION BY REFERENCE OF ADDITIONAL DISCLOSURES

Additional examples of system components and corrective methodology in accordance with various embodiments of the present invention are set forth in U.S. App. Pub. 2010/0318129, filed Jun. 16, 2009 and entitled "Deformity Alignment System with Reactive Force Balancing"; U.S. App. Pub. 2010/0249837, filed Mar. 26, 2009 and entitled "Semi-Constrained Anchoring System"; U.S. App. Pub. 2011/0054536, filed Sep. 1, 2010 and entitled "Growth Directed Vertebral Fixation System with Distractible Connector(s) and Apical Control"; U.S. Pat. No. 7,658,753, issued Feb. 9, 2010 and entitled "Device and Method for Correcting a Spinal Deformity"; and U.S. App. Pub. 2009/0012565, filed on Jun. 5, 2008 and entitled "Medical Device and Method to Correct Deformity," the entire contents of each of which are hereby incorporated by reference for all purposes.

BACKGROUND

Many systems have been utilized to treat spinal deformities such as scoliosis, spondylolisthesis, and a variety of others. Primary surgical methods for correcting a spinal deformity utilize instrumentation to correct the deformity as much as possible and separate implantable hardware systems to rigidly stabilize and maintain the correction.

SUMMARY

Some aspects relate to methods of correcting a spinal deformity, including securing a first rod on a first side of a spine, securing an anchor on a second side of the spine, securing a lateral coupling between the rod and the anchor, translating and derotating the spine to correct the spinal deformity by adjusting an effective length of the lateral coupling, and securing a second rod on the second side of the spine to provide secondary stabilization to the spine.

Some aspects relate to a system for correcting a spinal deformity, the system including first and second rods; first, second, third, and fourth anchors; and a lateral coupling. The first and second rods are adapted to extend along first and second sides, respectively, of a spine of a patient. The first anchor is adapted to be fixed to a vertebra of the spine and to receive the first rod such that the first rod is secured against substantial lateral translation relative to the first anchor and the first rod is allowed to slide axially relative to the first anchor through a first pivot point and to change in at least two of pitch, yaw, and roll about the first pivot point. The second anchor is also adapted to be fixed to a vertebra of the spine and to receive the first rod such that the first rod is secured against substantial lateral translation relative to the second stabilizing anchor and is allowed to change in at least pitch and yaw about a second pivot point. The third anchor is adapted to be fixed to a vertebra of the spine and to receive the second rod such that the second rod is secured against substantial lateral translation relative to the third anchor. The fourth anchor is adapted to be fixed to a vertebra of the spine and to receive the second rod such that the second rod is secured against substantial lateral translation relative to the fourth anchor. The lateral coupling is adapted to extend between and laterally secure the first rod and the second rod.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 4 is an isometric view of the stabilizing anchor of FIG. 3 with an insertion sleeve in a retention orientation, according to some embodiments.

FIG. 5 is a plan view of the stabilizing anchor of FIG. 3 with the insertion sleeve in the retention orientation, according to some embodiments.

FIG. 6 is an isometric view of the stabilizing anchor of FIG. 3 with the insertion sleeve in an insertion orientation, according to some embodiments.

FIG. 7 is a plan view of the stabilizing anchor of FIG. 3, with the insertion sleeve in the insertion orientation, according to some embodiments.

FIG. 12 is an isometric view of an actuation assembly of the system of FIG. 1, according to some embodiments.

FIG. 13 is a cross-section view of a portion of the actuation assembly of FIG. 12, according to some embodiments.

FIG. 14 is a bottom view of the actuation assembly of FIG. 12 with a portion of a clamshell housing removed, according to some embodiments.

FIG. 15 is a bottom view of the actuation assembly of FIG. 12, according to some embodiments.

FIG. 16 is a cross-sectional view of a connector head and tether of the actuation assembly of FIG. 12, according to some embodiments.

FIG. 17 is a cross-sectional view of the actuation assembly of FIG. 12, showing the connector head and tether in an extended state and a retracted state, according to some embodiments.

Figure 1:
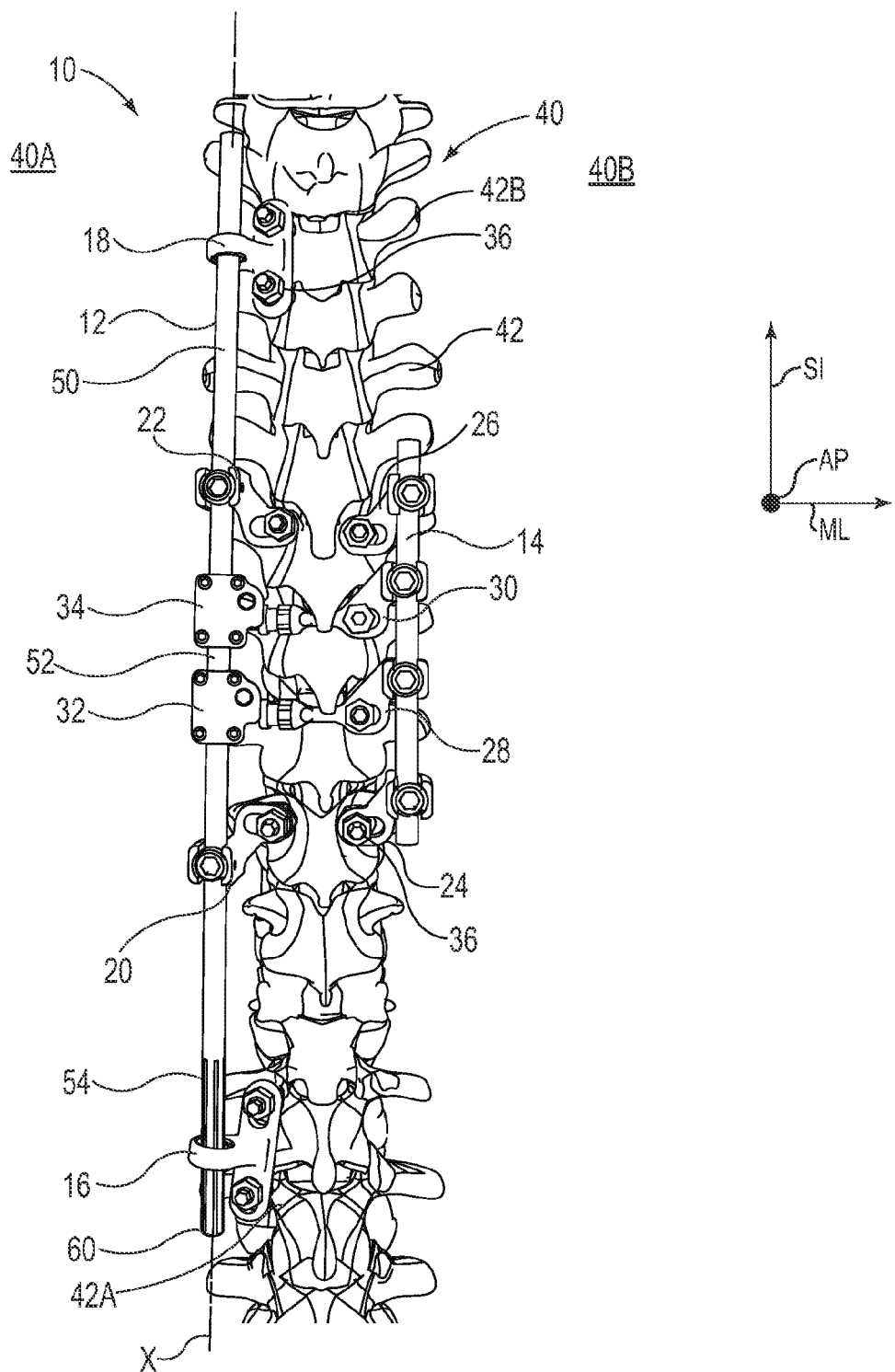
FIG. 1 is an isometric view of an implantable spinal correction and fusion system, according to some embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Some embodiments relate to a spinal correction and fusion system for implantation into a patient, as well as associated methods and devices. In general terms, the system provides for lateral translational corrective force(s) and/or derotational corrective force(s) on a spinal column with associated instrumentation for facilitating vertebral fusion at a selected region of the spine. Some features of the system include implementation of a first, relatively longer rod for initial correction, a second, shorter rod for secondary spinal stabilization. If desired, the secondary stabilization helps promote a fusion process. In some embodiments, the spine retains freedom of motion above and below the spinal segment corresponding to the shorter rod, with the first, relatively longer rod remaining implanted. In other embodiments, the first, relatively longer rod is trimmed and removed following correction of the spinal column and implementation of the second, shorter rod. A variety of additional features and advantages of the inventive systems are contemplated and provided by the instant disclosure.

FIG. 1 shows a spinal correction and fusion system 10, the system 10 including a first rod 12; a second rod 14; a plurality of anchors, including a first stabilizing anchor 16, a second stabilizing anchor 18, a first anchor 20, a second anchor 22, a third anchor 24, a fourth anchor 26; a first transverse anchor 28; a second transverse anchor 30; a first adjustment assembly 32; a second adjustment assembly 34; and a plurality of fasteners 36, such as bone screws, for securing components of the system 10 to a spine, or spinal column 40 having a first side 40A and a second side 40B. The system 10 is optionally used to bring the spine 40 to a more natural curvature (e.g., using a single adjustment). In other embodiments, an abnormal curvature in the spinal column 40 has been adjusted to a more natural curvature using other hardware, prior to or in conjunction with securing portions of the system 10 to the spinal column 40. In some embodiments, the system 10 is adapted to initially provide means for leveraged correction, with translation and derotation of the spine. If desired, the system 10 is adapted to provide means for selective fusion of the spine following correction. In other embodiments, the system 10 provides means for maintaining a correction to facilitate spine remodeling without vertebral fusion, or without permanent vertebral fusion.

Although the system 10 is shown with a select number of components, such as two stabilizing anchors 16, 18 two transverse anchors 28, 30, and two adjustment assemblies 32, 34, more or fewer are implemented as appropriate. For example, in some embodiments a single transverse anchor, such as the first transverse anchor 28, is secured to one or more of a plurality of vertebrae 42 at an apex A of a spinal deformation, with a corresponding adjustment assembly, such as the first adjustment assembly 32, coupled to the transverse anchor 28. Moreover, although four anchors 20, 22, 24, 26 are shown, in some embodiments there are more or less of the anchors. For example, in some embodiments the system 10 includes the first rod 12, the second rod 14, a single transverse anchor, such as the transverse anchor 28 and a single anchor, such as the third anchor 24, with the second rod 14 secured between the transverse anchor 28 and the third anchor 24. In still other embodiments, the system 10 does not include any of the anchors 20, 22, 24, 26, but instead the second rod 14 is secured between the first and second transverse anchors 28, 30 (see, e.g., FIG. 24). A variety of other configurations are also contemplated.

Various planes and associated directions are referenced in the following description, including a sagittal plane defined by two axes, one drawn between a head (superior) and tail (inferior) of the body and one drawn between a back (posterior) and front (anterior) of the body; a coronal plane defined by two axes, one drawn between a center (medial) to side (lateral) of the body and one drawn between a head (superior) and tail (inferior) of the body; and a transverse plane defined by two axes, one drawn between a back and front of the body and one drawing between a center and side of the body. The terms pitch, roll, and yaw are also used, where roll generally refers to angulation, or rotation, in a first plane through which a longitudinal axis of a body orthogonally passes (e.g., rotation about a longitudinal axis corresponding to the spinal column), pitch refers to angulation, or rotation, in a second plane orthogonal to the first plane, and yaw refers to angulation, or rotation, in a third plane orthogonal to the first and second planes. In some embodiments, pitch is angulation in the sagittal plane, yaw is angulation in the coronal plane, and roll is angulation in the transverse plane.

In various embodiments, changes in pitch, yaw, and/or roll occur concurrently or separately as desired. Moreover, as used herein, "lateral translation" is not limited to translation in the medial-lateral direction unless specified as such.

As shown in FIG. 1, in some embodiments the first rod 12, also described as an elongate member, is secured to the spinal column 40 at a pre-selected offset from a longitudinal axis of the spinal column 40. For example, the first rod 12 is optionally secured at an offset along a medial-lateral axis ML, or right-left axis, and anterior-posterior axis AP, or back-front axis. In some embodiments, the first rod 12 is secured on the left side of the spinal column 40 as shown. As subsequently described, the offset is optionally selected to cause at least a relative lateral translation (e.g., central or medial movement) and derotational shift of selected vertebrae 42 of the spinal column 40 (relative anterior-posterior movement of selected vertebrae 42 can also be accomplished) such that the spinal column 40 exhibits a more natural position.

Figure 20:
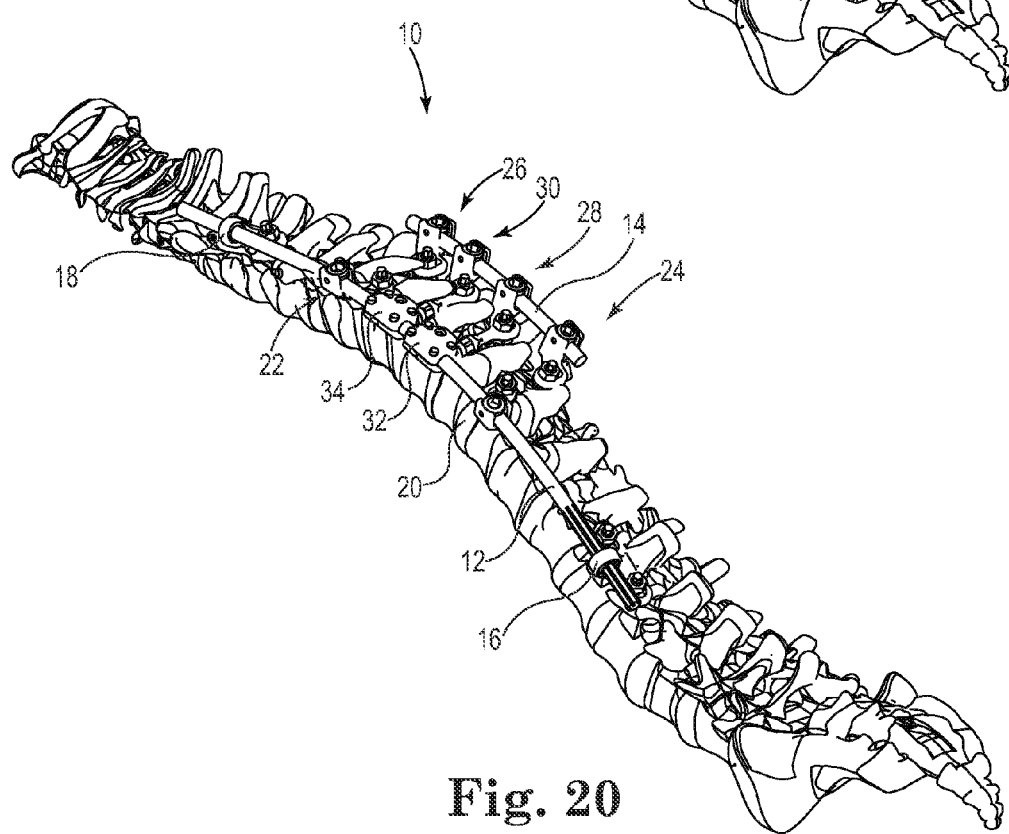

The first rod 12 is elongate and cylindrical including a superior portion 50, an intermediate portion 52, and an inferior portion 54. The first rod 12 is adapted, or otherwise structured, to extend along the spinal column 40. The first rod 12 is optionally contoured to complement a desired spinal curvature (e.g., generally following the curvature of a corrected, or natural spine as shown in FIG. 20). In some embodiments, the first rod 12 is substantially rigid, defining a substantially round cross-section with a mean diameter of about 6 mm and being formed of a suitable biocompatible material, such as titanium alloy ASTM F136, or cobalt chromium alloy ASTM F1537 or any other suitable implantable material. If desired, the first rod 12 incorporates some flex, or springiness while substantially rigidly retaining its shape. The first rod 12 is optionally formed of a variety of materials, including stainless steel or suitable polymeric materials.

The first rod 12 has a longitudinal axis X—where the rod 12 is substantially straight, the longitudinal axis X is substantially straight and, where the rod 12 is substantially curved or angled, the longitudinal axis X is similarly curved or angled. The sections 50, 52, 54 of the first rod 12 are optionally continuously formed or are formed as separate, connected parts as desired. In still other embodiments, expandable rod designs are also contemplated.

Figure 2:
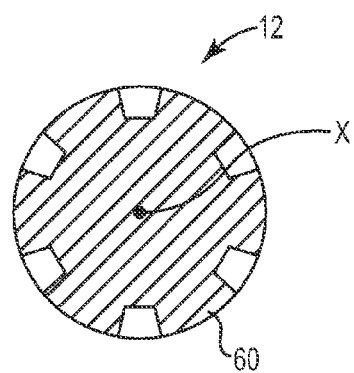
FIG. 2 is a cross-sectional view of a spinal rod of the system of FIG. 1, according to some embodiments.

FIG. 2 is a cross-sectional view of the first rod 12 in the inferior portion 54 of the first rod 12. As shown, the cross-sectional shape of the first rod 12, including various portions thereof, is not limited to circular cross-sections. For example, the inferior portion 54 optionally includes a plurality of splines 60 for mating with the first stabilizing anchor 16. As shown in FIG. 2, the splines 60 are trapezoidal (e.g., similarly to the teeth of a gear) with rounded bases, although a variety of shapes, such as involute shapes, are contemplated.

As shown in FIG. 1, the second rod 14 is substantially shorter than the first rod 12. For example, the second rod 14 is optionally configured (e.g., having a corresponding length and/or longitudinal contour) to extend along an apical region A of the spine 40 and/or between a desired number of anchors, such as the third and fourth anchors 24, 26. The second rod 14 is optionally formed of similar materials and with similar cross-section(s) to that of the first rod 12, as desired.

FIGS. 3 to 8 show the first stabilizing anchor 16 (also described as a rod anchor) of the system 10, according to some embodiments. As shown in FIG. 1, the first stabilizing anchor 16 is adapted, or otherwise structured, to be mounted, or fixed to one or more of the vertebrae 42, such as a first vertebra 42A (FIG. 1) located at an inferior position, or other position, along the spine 40.

Figure 3:
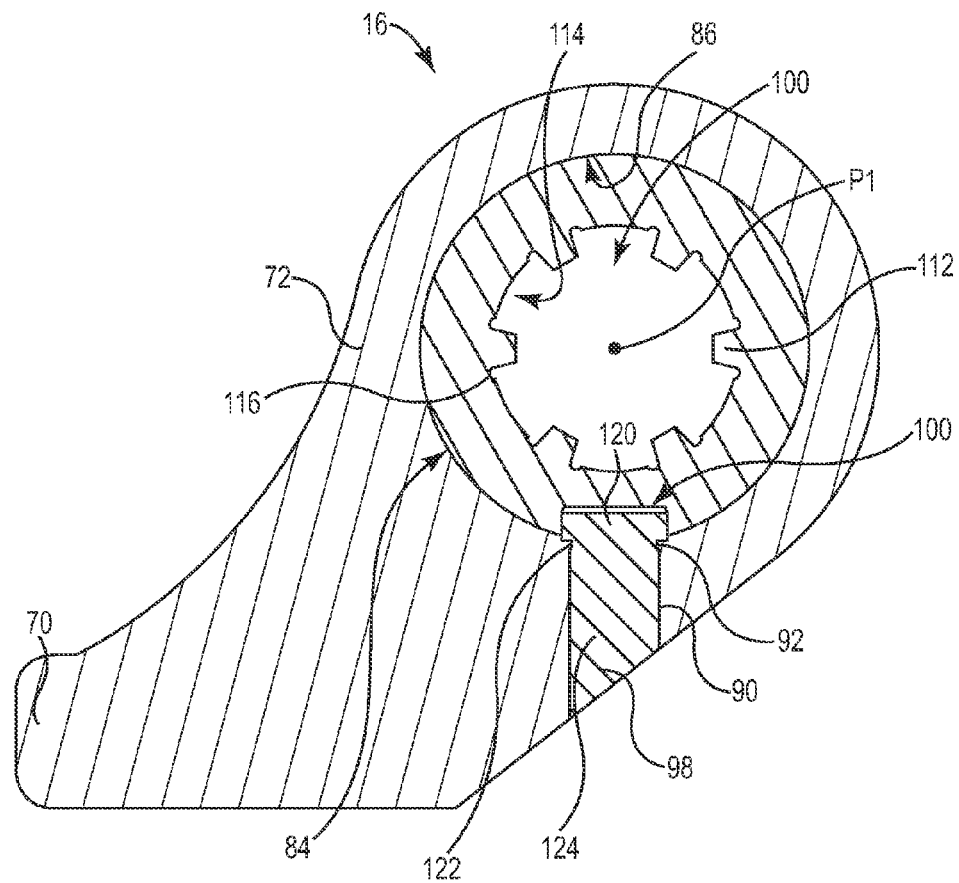
FIG. 3 is a cross-sectional view of a stabilizing anchor of the system of FIG. 1, according to some embodiments.

As shown in FIG. 3, the first stabilizing anchor 16 is adapted to receive, and includes means for receiving, the first rod 12 such that the first rod 12 is secured laterally, against lateral translation relative to the first stabilizing anchor 16. In some embodiments, the first rod 12 is substantially prevented from translating in a direction substantially perpendicular to the longitudinal axis X at a first pivot point P1. In turn, the first rod 12 is able to slide axially, or translate axially, along the longitudinal axis X of the first rod 12, relative to the first stabilizing anchor 16 through the first pivot point P1. The rod 12 is also able to change in pitch and yaw about the first pivot point P1. The first stabilizing anchor 16 is adapted, or otherwise structured, to limit rotation, or roll, of the first rod 12 about the longitudinal axis X of the first rod 12. In particular, the first stabilizing anchor 16 provides means for allowing the rod 12 to angulate without substantial lateral translation relative to the first stabilizing anchor 16 and without substantial rotation about the longitudinal axis X.

FIG. 4 is an isometric view of the first stabilizing anchor 16. As shown, the first stabilizing anchor 16 is optionally formed of biocompatible materials and includes a mounting portion 70 and a housing portion 72. The mounting portion 70 is adapted to secure the first stabilizing anchor 16 to one or more vertebrae 42, such as the first vertebra 42A and an additional vertebra 42 above or below the first vertebra 42A. In other embodiments, the mounting portion 70 is secured to a single vertebra, such as the first vertebra 42A (e.g., laterally across the first vertebra 70B at the pedicles, or at a single point—such as a single pedicle—on the first vertebra 26A. In some embodiments, the mounting portion 70, also described as a plate, is adapted to be secured at two or more points, for example spanning between two vertebrae 42 (e.g., the L3-L4 vertebrae) or spanning across a portion of a single vertebra 42 (e.g., pedicle-to-pedicle on a single vertebra).

In some embodiments, the mounting portion 70 includes a pedestal with first and second anchor locations, each of the anchor locations defining a surface suitable for mounting the first stabilizing anchor 16 to one or more vertebrae 42. The first and second anchor locations each optionally include through holes 74 for receiving one of the fasteners 36, such as a pedicle screw or similar device to secure the mounting portion 70 to one or more vertebrae 42, such as the first vertebra 42A.

The housing portion 72 of the first stabilizing anchor 16 includes a body 80 and a sleeve insert 82. In some embodiments, the sleeve insert 82 is substantially spherical in shape and the body 80 forms a substantially spherical mating race for receiving the sleeve insert 82. The body 80 has a sleeve aperture 84 (FIG. 5) extending front-to-back through the body 80, the sleeve aperture 84 defining a revolute, substantially concave articulation surface 86 (FIG. 5). The sleeve insert 82, in turn, forms a complementary revolute, substantially convex articulation surface 88. As shown in FIG. 3, the body 80 also has a pin chase 90 (e.g., a cylindrical through hole) that defines a terminal seat 92 having a larger diameter than a remainder of the pin chase 90.

Figure 8:
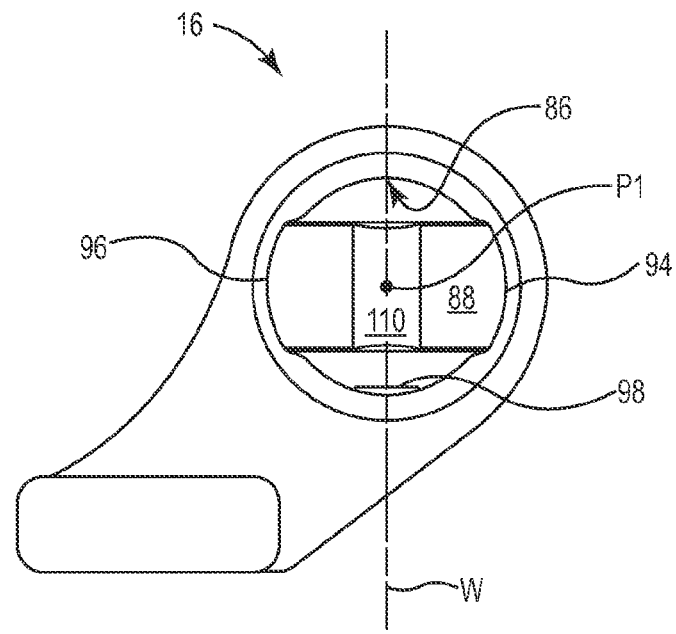
FIG. 8 is a front view of the stabilizing anchor of FIG. 3, with the insertion sleeve in the insertion orientation, according to some embodiments.

FIG. 5 is a plan view of the first stabilizing anchor 16, showing the sleeve insert 82 as it would be received within the body 80 (though normally hidden from view). As shown, the concave articulation surface 86 of the aperture 84 defines opposed apices 89 on each side of the articulation surface 86. The articulation surfaces 86, 88 are adapted, or otherwise structured, to form a substantially complementary fit with one another, such that the sleeve insert 82 is able to be captured by the body 80 within the aperture 94 and have relative angular movement with respect to the body 80. To facilitate assembly of the sleeve insert 82 into the body 80, the aperture 84 includes first and second channels 94, 96 formed into the articulation surface 86 at the apices 89 such that the minimum effective internal diameter D of the aperture 84 is increased between the channels 94, 96. The channels 94, 96 extend front to back through the body 80 and are positioned on opposite sides of the body 80. While two channels are shown, in other embodiments a single channel is included. FIG. 8 is a front view of the stabilizing anchor 16. As shown in FIGS. 5 and 8, the channels 94, 96 have arcuate profiles and extend into the aperture 84 to the apices 89 on each side of the articulation surface 86. The profiles of the channels 94, 96 are optionally complementary in shape to a portion of the profile—the lateral edges, or sides—of the sleeve insert 82 such that the sleeve insert 82 is able to be received through the channels 94, 96 into the aperture 84 when the sleeve insert 82 is oriented perpendicular, or edgewise relative to the body 80. The body 80 also includes a protrusion 98 (FIG. 3) (e.g., a pin) or protrusions (not shown) that extends inwardly into the aperture 84 from the articulation surface 86.

As shown in FIG. 3, the sleeve insert 82 has a passage 100 defining the pivot point P1 through which the splined, or inferior portion 54 of the first rod 12 is able to be slidably received. The sleeve insert 82 also has a groove 110 extending parallel to the center line of the sleeve insert into the convex articulation surface 88. The groove 110 is adapted to receive the protrusion 98 for limiting roll of the sleeve insert 82 within the body 80. The pivot point P1 is defined in the passage 100, where upon assembly the first rod 12 passes through the first pivot point P1 such that the longitudinal axis of the rod at the first pivot point P1 is generally concentric with the center of the passage 100.

As shown, the passage 100 has a non-circular cross-section (e.g., a splined cross-section corresponding to the inferior portion 54 of the first rod 12). Upon mating the non-circular cross-sections of the first rod 12 and the passage 100, rotation of the first rod 12 relative to the sleeve insert 82 is substantially inhibited or prevented. In some embodiments, the passage 100 defines a plurality (e.g., six) of inward splines 112 and a plurality of recessed pockets 114 (e.g., six) between the splines 112. The splines 112 are optionally trapezoidal (e.g., like the teeth of a gear) in shape overall. A variety of shapes are contemplated for the splines 112, including involute shapes, for example. The pockets 114 optionally include corner recesses 116 that are rounded in shape (e.g., to help prevent binding between the passage 100 and the first rod 112 during sliding of the first rod 112 in the passage 100). In some embodiments, the splines 60, 112 are designed to help maximize efficiency of torque transfer between the first rod 12 and the sleeve insert 82 while reducing contact pressure angle(s) between the components.

The protrusion 98 is optionally a pin with a head 120, a neck 122, and a body 124, the neck 122 being located between the head 120 and the body 124. The head 120, the neck 122, and the body 124 are optionally substantially cylindrical with the head 120 having a greater diameter than the body 124 and the body 124 having a greater diameter than the neck 122. The protrusion 98 is received in the pin chase 90 with the head 120 received in the seat 92 such that the head projects into the aperture 84. In some embodiments the protrusion 98 is press fit into the pin chase 90 and/or welded, adhered, or otherwise secured within the pin chase 90. In other embodiments the protrusion is temporary and is removable, providing temporary prevention of roll of the sleeve insert 82 within the body 80 so that the first stabilizing anchor 16 is able to be adjusted so that the rod 12 is free to rotate.

FIGS. 6, 7, and 8 show the sleeve insert 82 being assembled into the body 80 by positioning the sleeve insert 82 perpendicular, or edgewise, relative to the aperture 84 (FIG. 5) and sliding the sleeve insert 82 into the channels 94, 96. In other embodiments, the sleeve insert 82 is able to be inserted at another angle (45 degrees, for example). In this position, the diametric plane of the sleeve insert 82 is generally parallel to the centerline Z of the aperture 84. In alternate terms, the centerline W of the sleeve insert 82 is generally parallel to the diametric plane of the aperture 84. Once received in the aperture 84 via the channels 94, 96, the sleeve insert 82 is rotated such that the protrusion 98 (FIG. 3) is received in the groove 110 (e.g., as shown in FIGS. 3, 4, and 5). With the protrusion 98 slidably received in the groove 110, the pitch and yaw of the first rod 12 are still able to change while roll is substantially limited. The first rod 12 also remains free to slide axially within the sleeve insert 82, according to some embodiments.

As relative rotation between the sleeve insert 82 and the body 80 is also substantially inhibited, relative rotation between the first rod 12 and the first stabilizing anchor 16 is substantially inhibited or limited, allowing the first rod 12 to be maintained at a pre-selected rotational position relative to the first stabilizing anchor 16. It also should be understood that other cross-sectional shapes for each of the passage 100 (FIG. 3) and first rod 12 can be selected to allow some degree of rotation about the longitudinal axis X within a predefined range.

Figure 9:
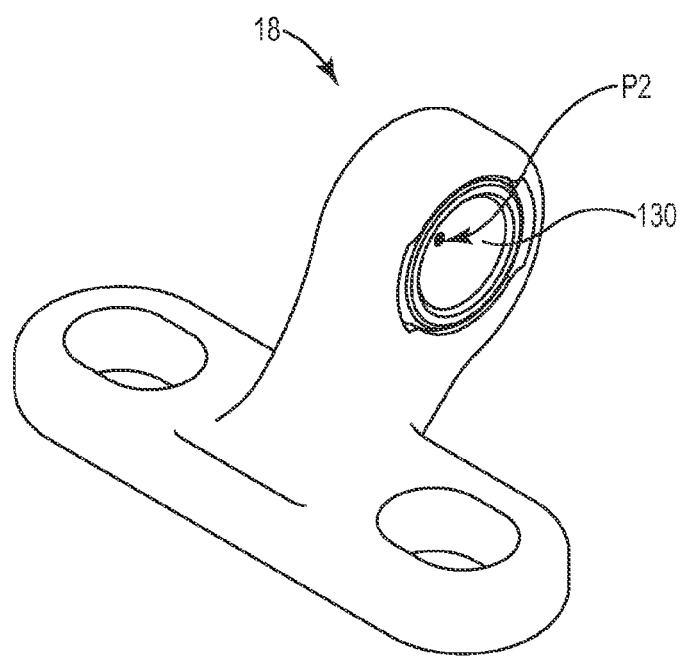
FIG. 9 is an isometric view of another stabilizing anchor of the system of FIG. 1, according to some embodiments.

In some embodiments, the second stabilizing anchor 18 is substantially similar to the first stabilizing anchor 16, including any desired combination of previously-described features. As shown in FIG. 9, the second stabilizing anchor 18 is substantially similar to the first stabilizing anchor 16, with the exception that the second stabilizing anchor 18 has a smooth bore 130 for receiving the first rod 12. The second stabilizing anchor 18 is adapted to be fixed, and provides means for fixation to a second vertebra, such as a second vertebra 42B (FIG. 1). The second stabilizing anchor 18 is further adapted to receive, and provides means for receiving the first rod 12 (FIG. 1) such that the second stabilizing anchor 18 limits translational movement of the first rod 12 except along the longitudinal axis X (i.e., the second stabilizing anchor 18 allows sliding movement of the first rod 12) and allows the first rod 12 to change in at least pitch and yaw about a second pivot point P2. Moreover, as shown the second stabilizing anchor 18 allows the first rod 12 to change in roll about the second pivot point P2.

Figure 10:
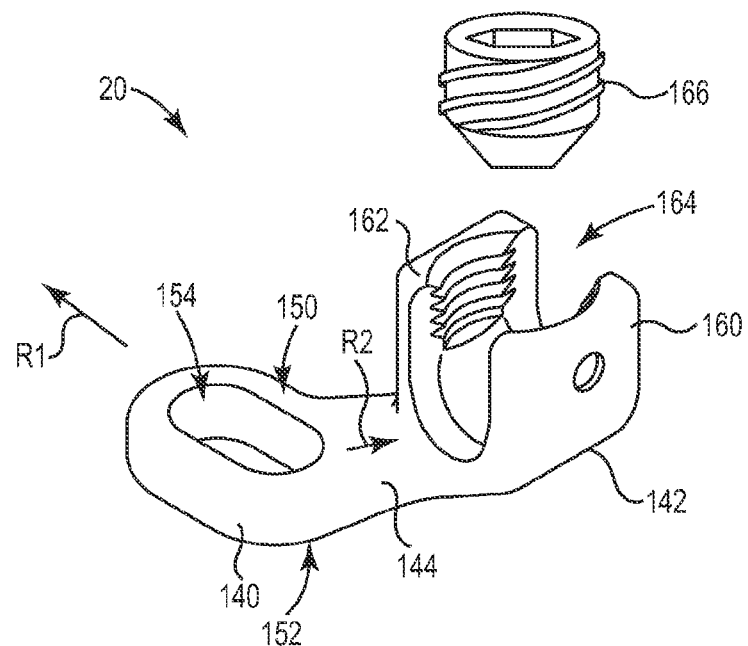
FIG. 10 is an isometric view of an anchor of the system of FIG. 1, according to some embodiments.

The first anchor 20 is shown in greater detail in FIG. 10, according to some embodiments. The first, second, third, and fourth anchors 20, 22, 24, 26 (FIG. 1) are optionally substantially similar, and thus various features of the anchors are described in association with the first anchor 20, where when referenced, features of the first anchor 20 are designated with reference numbers and similar features of the second, third, and fourth anchors 22, 24, 26 are designated with the same reference numbers followed by a "B," "C," and "D," respectively.

As shown, the first anchor 20 includes a mounting portion 140, a head portion 142, and a connection portion 144. The mounting portion 140 has a top surface 150, a bottom surface 152, and a slot 154 for receiving one of the fasteners 36, such as a pedicle screw or other bone screw. The slot 154, also described as an aperture, is elongate and extends longitudinally in a first direction R1.

The head portion 142 is substantially U-shaped, including a first prong 160 and a second prong 162 defining a pocket 164 for receiving one of the first and second rods 12, 14. As shown, the prongs 160, 162 are threaded for receiving a clamping screw 166 adapted to engage and secure one of the first and second rods 12, 14 immobilized within the pocket 164.

The connection portion 144 extends in a second direction R2 that is offset from the first direct R1. The connection portion 144 extends between the mounting portion 140 and the head portion 142 at an angle of about 45 degrees, for example, relative to the first direction R1.

The first and second transverse anchors 28, 30 are optionally substantially similar, and thus various features of both the first and second transverse anchors are described in association with the first transverse anchor 28, where when referenced, features of the first transverse anchor 28 are designated with reference numbers and similar features of the second transverse anchor 30 are designated with the same reference numbers followed by a "B."

Figure 11:
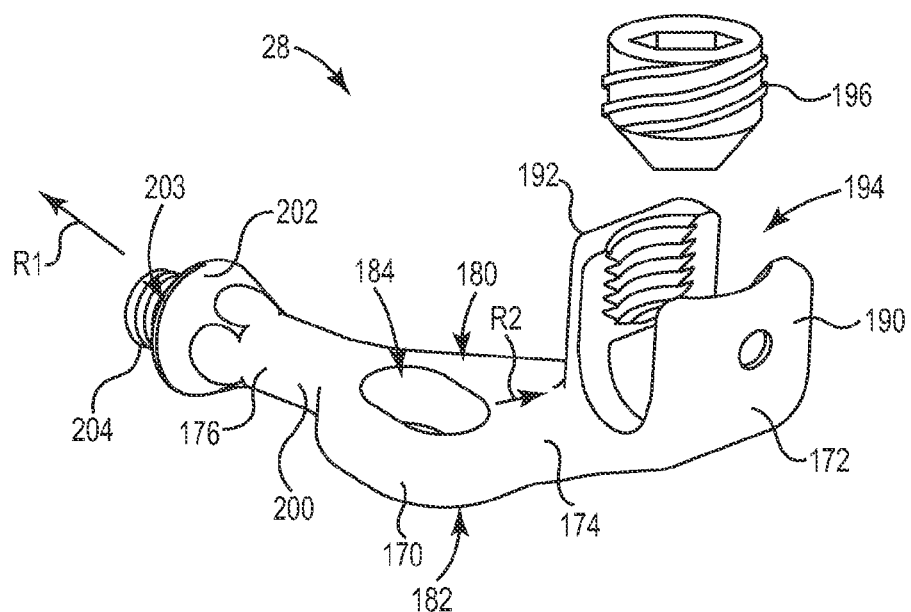
FIG. 11 is an isometric view of a transverse anchor of the system of FIG. 1, according to some embodiments.

The first transverse anchor 28 is shown in greater detail in FIG. 11, according to some embodiments. As shown, the first transverse anchor 28 includes a mounting portion 170, a head portion 172, a connection portion 174, and an arm portion 176. The mounting portion 170 has a top surface 180, a bottom surface 182, and a slot 184 for receiving one of the fasteners 36, such as a pedicle screw. The slot 184 is elongate and extends longitudinally in a first direction R1. In some embodiments, the arm portion 176 generally extends away from the mounting portion 170 for purpose of coupling to the first rod 12 and the head portion serves to couple the first transverse anchor 28 to the second rod 14.

The head portion 172 is substantially U-shaped, including a first prong 190 and a second prong 192 defining a pocket 194 for receiving the second rod 14. As shown, the prongs 190, 192 are threaded for receiving a clamping screw 196 adapted to engage and secure the second rod 14 immobilized within the pocket 194.

The connection portion 174 extends in a second direction R2 that is offset from the first direct R1. The connection portion 174 extends between the mounting portion 170 and the head portion 172 at an angle of about 45 degrees, for example, relative to the first direction R1. In other embodiments, the connection portion 174 extends between the mounting portion and head portion 170, 172 at another angle, such as from about 30 to about 60 degrees, or at no angle (i.e., the portions 170, 172, 174 are generally in-line with one another).

The arm portion 176 includes a neck section 200 that is substantially elongate and cylindrical, a shoulder section 202 that is flared and defines an abutment face 203, and a terminal section 204 that is threaded. The arm portion 176 extends longitudinally in the first direction R1. The arm portion 176 is adapted to extend across a portion of one of the vertebrae 42 for example, from one side of the spinal column 40 to an opposite side of the spinal column 40. For example, the first transverse anchor 28 is secured to one of the vertebrae 42 such that the arm portion 176 extends laterally across the vertebra 42.

FIG. 12 shows the first adjustment assembly 32 from an isometric view, FIG. 13 shows the adjustment 32 assembly from a cross-sectional view, FIG. 14 shows the adjustment assembly 32 from a plan view with a portion of the housing removed, and FIG. 15 shows the adjustment assembly 32 from a plan view with the housing intact, according to some embodiments.

The first adjustment assembly 32 is adapted to adjust, and provides means for adjusting tension and/or a distance between the first rod 12 and the first transverse anchor 28. The first and second adjustment assemblies 32, 34 are optionally substantially similar. Thus, various features of both the first and second adjustment assemblies 32, 34 are described in association with the first adjustment assembly 32, where features of the first adjustment assembly 32 are designated with reference numbers and similar features of the second adjustment assembly 34 are designated with the same reference numbers followed by a "B."

As shown, the first adjustment assembly 32 includes a tensioner 208, the tensioner 208 including a housing 210, a reel 212, a circumferential gear 214 surrounding the reel 212, a drive gear 216 in contact with the circumferential gear 214, and an actuation head 218. The first adjustment assembly 32 also includes an elongate connector 219 adapted to be wound about the reel 212.

The reel 212, as well as the circumferential gear 214 and drive gear 216 are maintained at least partially within the housing 210. In turn, the housing 210 is adapted to be secured to the first rod 12. For example, the housing 210 optionally forms a central lumen 220 through which the rod first 12 is receivable. Upon inserting the first rod 12 through the central lumen 220, the housing 210 is adapted to be clamped onto the first rod 12.

In some embodiments, the housing 210 defines a first side 223 and a second side 224 and incorporates a clamshell design (e.g., a first portion adjustably secured to a second portion) adapted to be tightened onto the first rod 12 (e.g., using one or more fasteners). Thus, in some embodiments, the first adjustment assembly 32 is substantially fixed with respect to the first rod 12. Other designs, such as monolithic housing designs and others are contemplated. Moreover, in some embodiments, the first adjustment assembly 32 is movable with respect to the first rod 12, for example being able to slide and/or rotate about the first rod 12.

The central lumen 220 of the housing 210 defines a longitudinal axis L and forms a pocket 226 for receiving the reel 212 and the circumferential gear 214 such that the reel 212 and the circumferential gear 214 are able to rotate within the housing 210. The housing 210 also defines a pair of opposed apertures 228 for receiving ends of the drive gear 216 to retain the drive gear 216 while allowing the drive gear 216 to rotate. As shown, the housing 210 also defines a top 230 and a bottom 232, where the bottom 232 forms a lower opening 234 and a raised abutment 236 adjacent to the lower opening 234, toward the first side 223 of the housing 210.

As shown, the reel 212 includes a helical groove 238 for receiving the elongate connector 219 and a raised anchor block 240 for securing the elongate connector 219 to the reel 212. For example, the anchor block 240 optionally includes an aperture for receiving the elongate connector 219 and is welded or otherwise fastened in the aperture. The reel 212, as well as the circumferential gear 214, form a lumen 242 for coaxially receiving the first rod 12. In some embodiments, by receiving the first rod 12 through the reel 212 and circumferential gear 214, an overall size, or profile, of the tensioner 208 is able to be reduced.

As shown, the circumferential gear 214 is connected to, and coaxially aligned with the reel 212. The circumferential gear 214 is engaged with the drive gear 216 such that rotation of the drive gear 216 causes the circumferential gear 214, and thus, the reel 212, to turn (e.g., in a worm or crossed-spur gear configuration).

The elongate connector 219 includes a flexible tether 250 and a connector head 252. In some embodiments, the flexible tether 250 is substantially flexible and able to be pivoted in a multiple directions and/or be spooled or wound, for example. Suitable flexible materials include wire and stranded cables, monofilament polymer materials, multifilament polymer materials, multifilament carbon or ceramic fibers, and others. In some embodiments, the flexible tether 250 is formed of cobalt chromium alloy or titanium alloy wire or cable, although a variety of materials are contemplated. The flexible tether 250 includes a terminal cap 256 (FIG. 16) adapted to be secured in the connector head 252. The terminal cap 256 has a rounded (e.g., semi-circular) head and is optionally swaged onto the flexible tether 250. In other embodiments, rather than a swage a loop or other feature is implemented to connect of the connector head 252.

FIG. 16 is a cross-sectional view of the connector head 252, according to some embodiments. As shown, the connector head 252 defines an internal bore 260 and forms a collar 262, a raised shoulder 264, and a neck 266. The internal bore 260 has a rounded seat 270 (e.g., a substantially concave seat). The connector head 252 also has a first end 272 and a second end 274, the second end 274 having a rounded inner profile 276 (like the horn of a trumpet). The flexible tether 250 is secured to the connector head 252 by receiving the terminal cap 256 in the rounded seat 270 in a complementary fit.

The elongate connector 219, also described as a connector or cable, is adapted to be secured to the first transverse anchor 28 and the first adjustment assembly 32. So secured, the elongate connector 219 defines an effective length between the first transverse anchor 28 and tensioner 208 and, and thus the first rod 12 (although, in some embodiments, the elongate connector 219 is secured directly to the rod 12). As described, in some embodiments, the tensioner 208 is adapted to modify, and provides means for modifying, the effective length of the tether 250 of the elongate connector 219 (e.g., by spooling the tether 250 on and off of the reel 212).

The elongate connector 219 is attached or secured to the reel 212 and passes out of the housing 210 through the lower opening 234 in the housing 210. Although a lower opening is shown, in other embodiments the opening is in the side or top, for example. Actuation of the drive gear 216 via the actuation head 218 turns the circumferential gear 214, which turns the reel 212, thus winding (or unwinding, depending on the direction in which the reel 212 is turned) the elongate connector 219 about the reel 212. Rotation of the reel 212 in the appropriate direction draws the tether 250 in toward the tensioner 208 (FIG. 17), pulling the first transverse anchor 28 toward the tensioner 208, according to some methods of correcting a spinal defect.

FIG. 17 shows the first actuation assembly 32 as it would appear in a first, extended state attached to the uncorrected spinal column 40 (e.g., FIG. 18) and as it would appear in a second, retracted state as attached to the corrected spinal column (e.g., FIG. 19), according to some embodiments. As shown, the connector head 252 engages the raised abutment 236 and the housing 210 as the tether 250 is drawn into the housing 210. This engagement and/or the orientation of the lower opening 234 (i.e., with the tether 250 exiting the housing 210 through the bottom) helps generate a moment M on the first transverse anchor 28 (not shown in FIG. 17) thereby helping to derotate the third vertebra 42C to which the first transverse anchor 28 is attached. The ability of the tether 250 to flex and bend at the second end 274 of the connector head 252 helps generate a polyaxial connection at the second end 274 and facilitates generation of the moment M as described.

Figure 18:
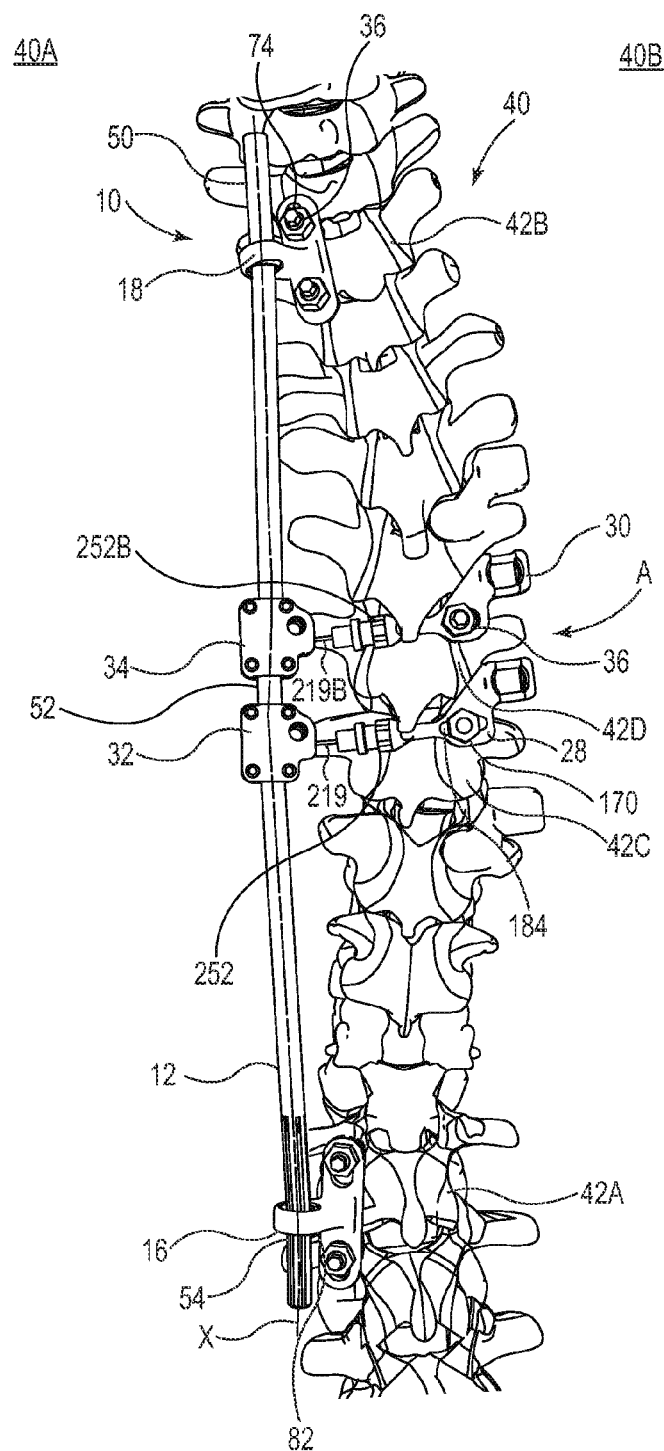
FIG. 18 is an isometric view of the system of FIG. 1 during a correction procedure, according to some embodiments.

FIG. 18 shows the assembled system 10. In some embodiments, assembly of the system 10 and associated methods of correcting the spine 40 include securing the stabilizing anchors 16, 18 to inferior and superior portions of the spine 40. For example, the first stabilizing anchor 16 is optionally secured to the spine 40 by driving one of the plurality of fasteners 36 through each of the through holes 74 and into one or more of the vertebrae 42. For example, as shown in FIG. 1, the first stabilizing anchor 16 is secured with one of the fasteners 36 driven into a pedicle of the first vertebra 42A and another of the fasteners 26 driven into a pedicle of another vertebra that is adjacent to the first vertebra 42A. The second stabilizing anchor 18 is similarly secured to the second vertebra 42B and a vertebra adjacent the second vertebra 42B. As shown, each of the first and second stabilizing anchors is secured on the first side 40A of the spine.

The first and second actuation assemblies 32, 34 are slid onto or otherwise coupled to the first rod 12 and then secured (e.g., clamped) at a desired location along the rod 12. The first rod 12 is received in the first and second stabilizing anchors 16, 18, with the splined, or inferior portion 54 of the first rod 12 slidably received in the sleeve insert 82 of the first stabilizing anchor 16 and the superior portion 50 of the rod 12 slidably received in the second stabilizing anchor 18. Thus, in some embodiments the first rod 12 extends along the first side 40A of the spine 40 and is secured against lateral movement relative to a portion of the spine 40.

In some embodiments, the first rod 12 is attached by the stabilizing anchors 16, 18 to pedicles and/or transverse processes on the first side 40A of the spinal column 40 and is able to slide axially relative to the first and/or second stabilizing anchors 16, 18. In other embodiments, the rod 12 is attached by the stabilizing anchors 16, 18 to the second side 40B of the spinal column 40, on different sides of the spinal column 40 (e.g., the first stabilizing anchor 16 on the left side and the second stabilizing anchor 18 on the right side), or along the mid-line of the spinal column 40. In other embodiments, the first rod 12 is adjustable length to compensate for changes in length of the spinal column 40.

By limiting rotation, or roll, of the first rod 12 relative to the first stabilizing anchor 16, the bend in the first rod 12 is oriented and maintained in a desired rotational position. Maintaining the rotational orientation at one end (i.e., at the first stabilizing anchor 16) is useful, for example, to help ensure that the bend or shape of the rod 12 consistently follows or otherwise appropriately tracks a desired curvature of a spinal column 40. Freedom of rotation at the other end of the first rod 12 (i.e., at the second stabilizing anchor 18), however, still permits the spinal column 40 to have more natural movement while the corrective forces are being applied.

Though not shown, the system 10 optionally includes one or more stop features for limiting axial sliding, or translation of the first rod 12 relative to one of the stabilizing anchors to a desired range. Generally, sliding of the first rod 12 in a particular axial direction is substantially limited, or arrested, when a stop feature engages, or abuts an adjacent stabilizing anchor 16, though other stop mechanisms are contemplated.

The first and second transverse anchors 28, 30 are secured to one or more of the vertebrae 42, such as a third vertebra 42C in an apical region A of the spine 40 and a fourth vertebra 42D in an apical region A of the spine 40. The first transverse anchor 28 is secured to the third vertebra 42C by driving one of the fasteners 36 through the slot 184 in the mounting portion 170 of the first transverse anchor 28. For example, the first transverse anchor 28 is optionally secured into a pedicle and/or transverse processes of the third vertebra 42C on the second side 40B of the spine 40. The second transverse anchor 30 is optionally similarly secured on the second side of the spine 42B to a pedicle of the fourth vertebra 42D. As shown, the arm portions 176, 176B (FIG. 11) of the first and second transverse anchors 28, 30 extend from the second side 40B of the spine 40 to the first side 40A of the spine 40.

The first and second actuation assemblies 32, 34 are secured to the first and second transverse anchors 28, 30 by attaching (e.g., screwing) the connector heads 252, 252B of the elongate connectors 219, 219B to the threaded terminal sections of the transverse anchors 28, 30. Some methods include adjusting a curvature of the spine 40 to a desired curvature using the actuation assemblies 32, 34. For example, the tensioners 208, 208B of the first and second actuation assemblies 32, 34 are actuated (independently or simultaneously) in order to draw the elongate connectors 219, 219B into the respective tensioners 208, 208B, thereby drawing the third and fourth vertebrae 42C, 42D and surrounding portions of the spine 40 toward the first rod 12 and to a more desirable spinal curvature.

Figure 19:
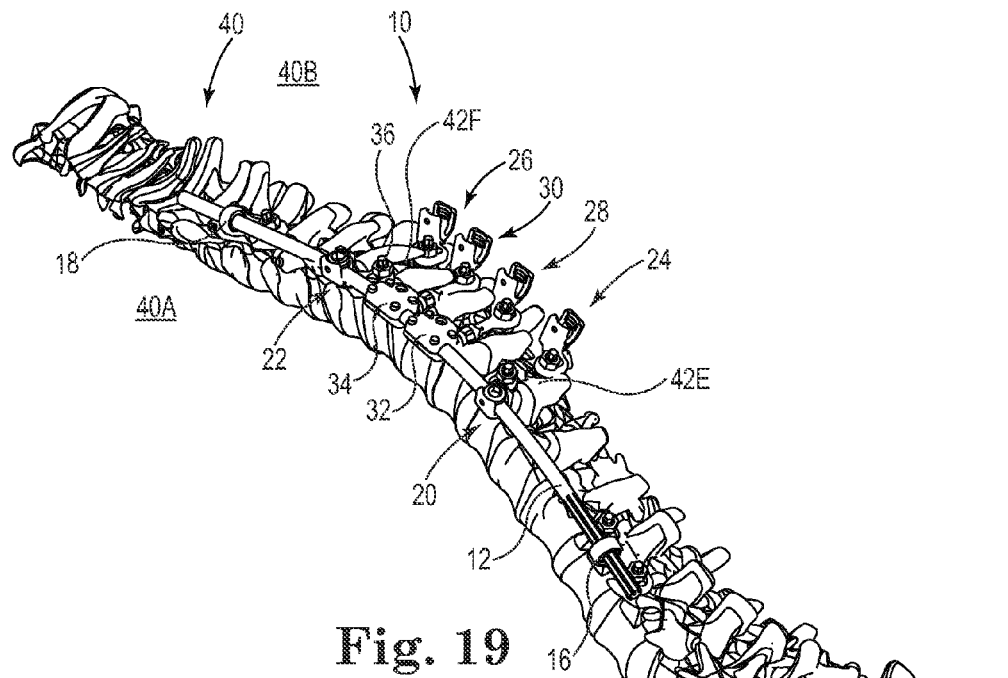
FIGS. 19 and 20 are isometric views of the system of FIG. 1 before and after assembly of a second rod into the system, according to some embodiments.

As shown in FIG. 19, the first and third anchors 20, 24 are secured to a fifth vertebra 42E and the second and fourth anchors 22, 26 are secured to a sixth vertebrae 42E, 42F of the spine 40, thought each of the connectors is optionally secured to a different vertebra. The first anchor 20 is secured along the spine 40 at a location between the first stabilizing anchor 16 and the first actuation assembly 32 and the second stabilizing anchor 18 is secured at a location between the second stabilizing anchor 18 and the second actuation assembly 34. The first and second anchors 20, 22 are secured on the first side 40A of the spine 40 whereas the third and fourth anchors 24, 26 are secured on the second side 40B of the spine 40 opposite the first and second anchors 20, 22, for example. The first anchor 20 is secured to a pedicle of the fifth vertebra 42E by driving one of the fasteners 36 into the pedicle through the slot 154 in the mounting portion 140 of the first anchor 20 (FIG. The second, third, and fourth anchors 22, 24, 26 are optionally similarly secured to the spine 40.

If desired, the first rod 12 is received in the first and second anchors 20, 22 (e.g., prior to securing the first and second anchors 20, 22 to the spine 40) and the first rod 12 is secured in the pocket 164 of the first anchor 20 using the clamping screw 166 (FIG. 10). The first rod 12 is similarly secured in the second anchor 22, thereby immobilizing the first rod 12 between the first and second anchors 20, 22.

As shown in FIG. 20, the second rod 14 is received in the transverse anchors 28, 30, and optionally in the third and fourth anchors 24, 26 (e.g., prior to securing the third and fourth anchors 24, 26 to the spine 40) in order to provide secondary stabilization to the corresponding region of the spine 40. For example, the second rod 12 is secured in the pocket of the third anchor 24 using the clamping screw and in the pocket 194 of the first transverse anchor 28 using the clamping screw 196 (FIG. 11). The second rod 14 is similarly secured in the second transverse anchor 30 and the fourth anchor 26, thereby immobilizing the second rod 14 between the third and fourth anchors 24, 26. As shown, the first and second rods 12, 14 are on opposite sides of the spine 40, immobilizing a desired region of the spine 40 (e.g., as part of a spinal fusion process), such as an apical region A of the spine 40. As appropriate, bone cement, fillers, or other materials are optionally employed with one or more vertebrae 42 to facilitate intervertebral fusion. In other embodiments, the system 10 is configured to avoid fusion of the spine 40. For example, the first and/or second rods 12, 14 are optionally substantially flexible such that the system 10 allows sufficient movement of the spine 40 to help avoid intervertebral fusion while still providing structural support during growth and remodeling of the spine 40.

Figures 21, 22, 23:
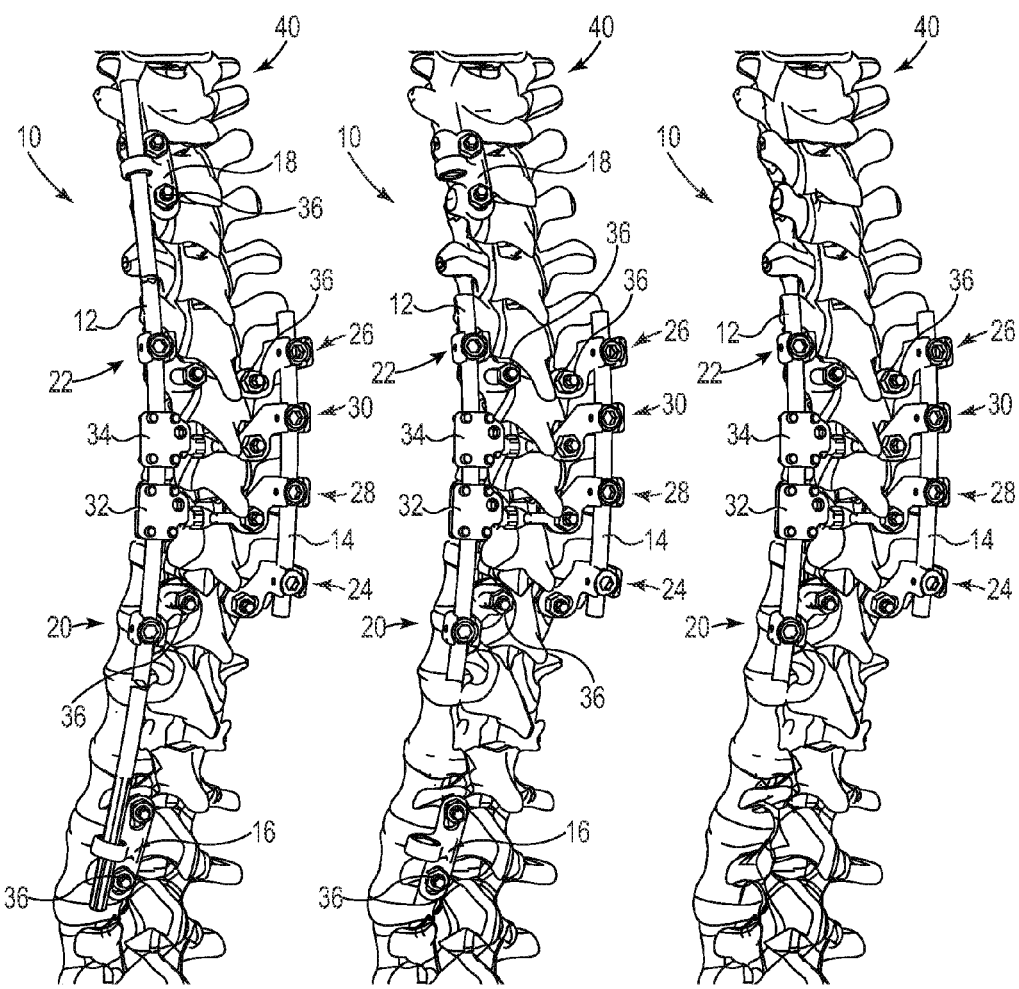
FIGS. 21 to 23 are isometric views of the system of FIG. 1 showing a process of separating and removing portions of the first rod and stabilizing anchors, according to some embodiments.

As shown in FIG. 21, if desired (e.g., once the spine 40 is stabilized), the first rod 12 is clipped, cut, broken, or otherwise portioned between the first anchor 20 and the first stabilizing anchor 16 and between the second anchor 22 and the second stabilizing anchor 18. As shown in FIG. 22, the superior and inferior portions of the first rod 12 are optionally removed from the first and second stabilizing anchors 16, 18 and the first and second stabilizing anchors 16, 18 are removed from the spine 40. As another alternative, the first rod 12 is not portioned and is left free to move in the stabilizing anchors 16, 18, for example. Moreover, if desired, the entire system 10 is optionally removed after a desired amount of fusion of the spine has been achieved and/or after sufficient growth and remodeling of the spinal curvature has been achieved. For example, once a diseased area of the spine has sufficiently healed (e.g., after being fused and stabilized) the stability provided by the system 10 may no longer be required.

Thus, according to various embodiments, the spinal column 40 (and thus, the person) is able to twist, bend side-to-side, and bend forward-and-backward in a more natural manner while corrective forces are being applied to the spinal column 40 and/or to achieve a desired correction of the spine 40. In some embodiments, the effective lengths of the actuation assemblies 34, 36, and specifically the elongate connectors 219, 219B are adjusted (e.g., periodically or all at one time), bringing the spinal column into natural alignment, while the system 10 facilitates a more natural movement of the spinal column 40 (e.g., twisting and bending forward-and-backward and side-to-side) due to the freedom of movement afforded by the system 10. During a secondary fusion procedure, the second rod 14 is secured to the corrected spine 40 opposite first rod 12 to rigidly secure a region of the spine for fusion as shown in FIG. 23. If desired, this includes immobilizing an apical region A of the spine 40 and leaving a superior region of the spine 40 adjacent to the apical region A and an inferior region of the spine 40 adjacent to the apical region A free to move in at least one degree of freedom. The at least one degree of freedom optionally includes elongation, or growth, compression, twisting, and/or flexing. In some embodiments, the freedom of movement of the first rod 12 provided by the stabilizing anchors 16, 18 helps facilitate this motion. In other embodiments, removal of one or more portions of the system 10 (e.g., clipping and removing portions of the rod 12) facilitates this motion.

In some embodiments, by linking the convex and concave sides of the spine 40 together, stress on the spine 40 is distributed at the anchor-vertebral interfaces as well as stiffening the apical region A of the spine, helping to stabilize the deformity. Thus, in addition to the connection between the apical region A and the first rod 12, the lateral connection between the rods 12, 14 optionally helps resist vertebral rotation and lateral translation).

As previously indicated, in some embodiments, the spine 40 is optionally corrected, or tensioned toward the first rod 12 prior to securing the second rod 14 to the spine 40. In other embodiments, the corrective method includes securing the second rod 14 to the spine 40 (e.g., to partially or fully correct spinal curvature the apical region A) and then tensioning the second rod 14 toward the first rod 12 in order to correct the spine 40 or portions thereof (e.g., a curvature of the spine 40 superior and/or inferior to the apical region A).

Figure 24:
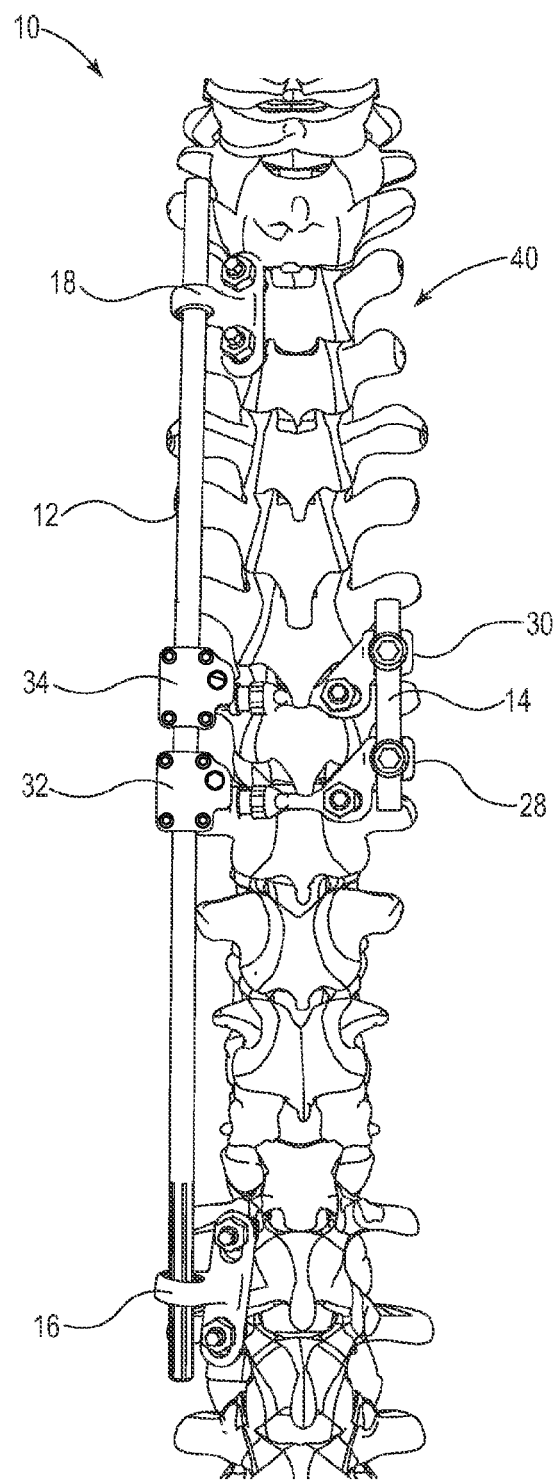
FIG. 24 is an isometric view of a system of another configuration, according to some embodiments.

As previously indicated, the system 10 may include greater or fewer components according to various embodiments. FIG. 24 is an example of the system 10, which includes correction and secondary stabilization features, the system 10 including fewer components. With reference to FIG. 18, the system 10 is optionally used to correct a spinal deformity (including a total or partial correction) and then the second rod 14 is received in, and secured in, the pockets 194, 194B of the first and second transverse anchors 28, 30. The secondary stabilization provided by the second rod 14 is optionally used to facilitate fusion of the spine 40, including use of growth promoters or other materials for encouraging intervertebral fusion.

Figure 25:
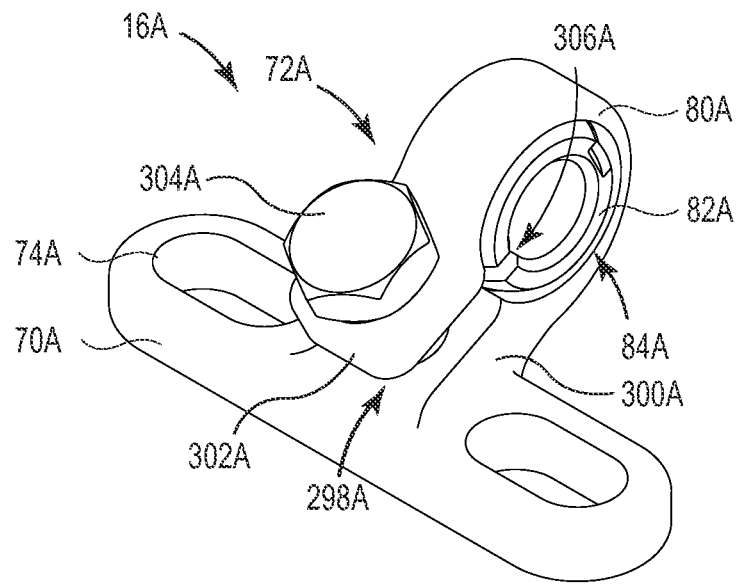
FIG. 25 is an isometric view of another anchor of an implantable spinal correction and fusion system, according to some embodiments.

FIG. 25 shows another stabilizing anchor 16A (also described as a rod anchor) of the system 10, according to some embodiments. The first stabilizing anchor 16A is adapted, or otherwise structured, to be mounted, or fixed to one or more of the vertebrae 42, such as a first vertebra 42A (FIG. 1) located at an inferior position, or other position, along the spine 40.

As shown, the first stabilizing anchor 16A is substantially similar to the first stabilizing anchor 16. The first stabilizing anchor 16A includes a mounting portion 70A and a housing portion 72A. The mounting portion 70A optionally includes through holes 74A for receiving one of the fasteners 36, such as a pedicle screw or similar device to secure the mounting portion 70A to one or more vertebrae 42, such as the first vertebra 42A.

The housing portion 72A of the first stabilizing anchor 16A includes a body 80A and a sleeve insert 82A. The body 80A is substantially similar to the body 80 of the first stabilizing anchor 16 with an optional difference being that the body 80A is split by a gap 298A dividing the body 80A into a lower portion 300A and an upper portion 302A that can be clamped together with adjustment member 304A (e.g., a bolt) secured across the gap 298A. The sleeve insert 82A, in turn, is substantially similar to the sleeve insert 82 with the addition of a gap 306A that facilitates clamping of the sleeve insert 82A onto the rod 12. For example, upon sufficiently tightening the adjustment member 304A, the sleeve insert 82A is clamped onto rod 12 to arrest sliding and rolling motion of the rod 12 through the sleeve insert 82A. Additionally, the clamping action of the body 80A on the sleeve 82A arrests changes in pitch and yaw. In different terms, the rod 12 is able to be selectively locked relative to the stabilizing anchor 16A.

Figure 26:
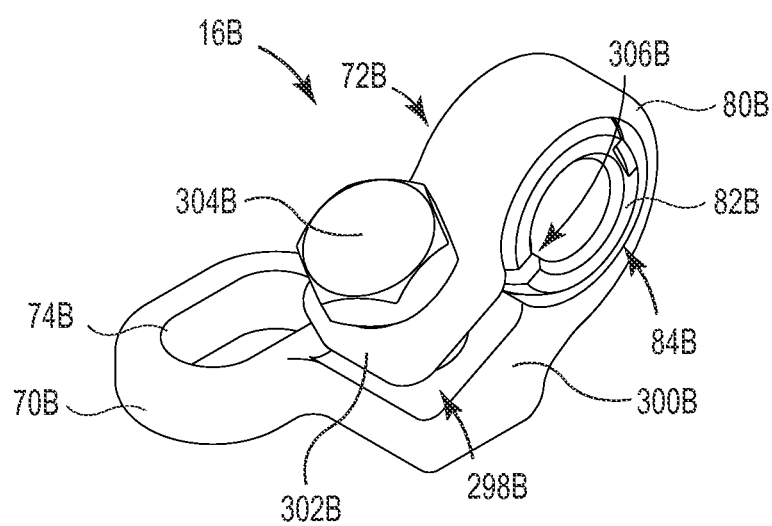
FIG. 26 is an isometric view of another anchor of an implantable spinal correction and fusion system, according to some embodiments.

FIG. 26 shows another stabilizing anchor 16B (also described as a rod anchor) of the system 10, according to some embodiments. The first stabilizing anchor 16B is adapted, or otherwise structured, to be mounted, or fixed to one or more of the vertebrae 42, such as a first vertebra 42A (FIG. 1) located at an inferior position, or other position, along the spine 40.

As shown, the first stabilizing anchor 16B is substantially similar to the first stabilizing anchors 16, 16A and includes a clamping mechanism similar to first stabilizing anchor 16A. The first stabilizing anchor 16B includes a mounting portion 70B and a housing portion 72B. The mounting portion 70B differs from the mounting portion 70A of the first stabilizing anchor 16A in that the mounting 70B portion includes a single through hole 74A for receiving one of the fasteners 36, such as a pedicle screw or similar device to secure the mounting portion 70B to one or more vertebrae 42, such as the first vertebra 42A. In some embodiments, the first stabilizing anchor 16B is adapted to be secured to a single vertebra, as compared to being secured across multiple vertebrae.

Figures 27, 28:
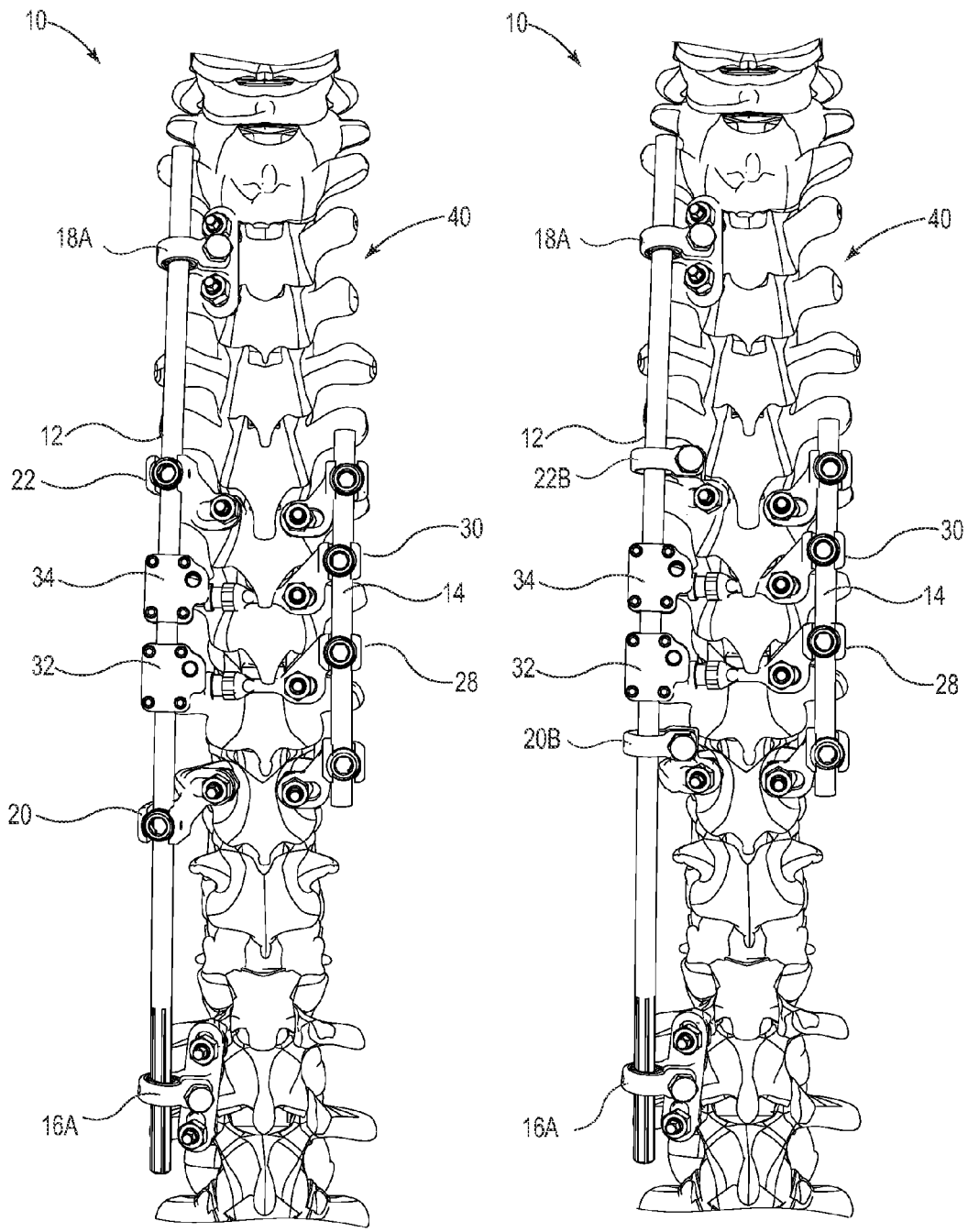
FIG. 27 shows another configuration for an implantable spinal correction and fusion system, according to some embodiments.
FIG. 28 shows another configuration for an implantable spinal correction and fusion system, according to some embodiments.

FIG. 27 shows the system 10 employing the first stabilizing anchor 16A and a second stabilizing anchor 18A that is substantially the same as the first stabilizing anchor 16A, according to some embodiments. As shown in FIG. 27, the rod 12 of the system 10 is able to slide and change in pitch, yaw, and roll at both of the anchors 16A, 18A and is also able to be selectively locked against sliding, pitch, yaw, and roll at each of the first and second stabilizing anchors 16A, 18A. Selective locking at one or both anchors 16A, 18A is optionally employed for a variety of reasons, including for performing partial or total fusion, to facilitate a correction, or adjustment process using the tensioners 32, 34, or to facilitate assembly of the system 10 prior to a correction operation.

FIG. 28 shows the system 10 employing the first and second stabilizing anchors 16A, 18A similarly to FIG. 27, according to some embodiments. In addition, the first anchor 20 and the second anchor 22 shown in FIG. 27 are replaced by first and second anchors 20B, 22B, which are each substantially the same as the first stabilizing anchor 16B (FIG. 26). As shown in FIG. 28, the rod 12 of the system 10 is able to slide and change pitch, yaw and roll at the anchors 16A, 18A, 20B, 22B and is also able to be selectively locked against sliding, pitch, yaw, and roll at each of the anchors 16A, 18A, 20B, 22B as desired. Once again, selective locking at any of the anchors 16A, 18A, 20B, 22B is optionally employed for a variety of reasons, including for performing partial or total fusion, to facilitate a correction, or adjustment process using the tensioners 32, 34, or to facilitate assembly of the system 10 prior to a correction operation.

Figure 29:
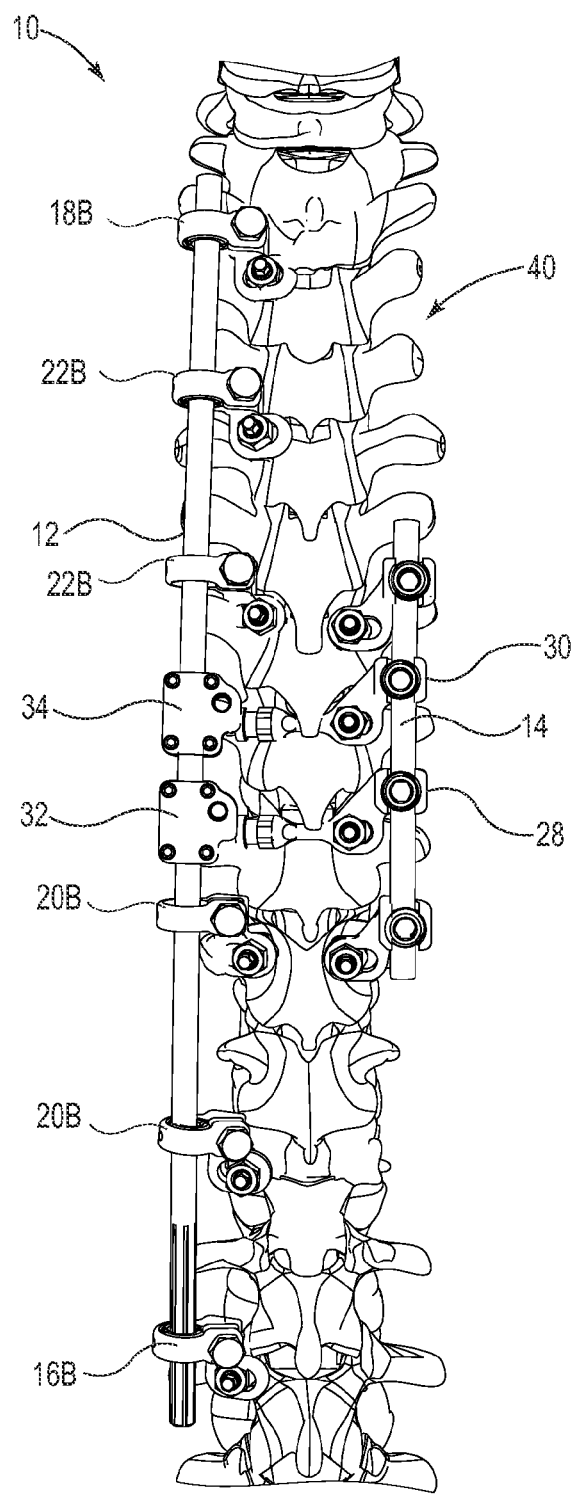
FIG. 29 shows another configuration for an implantable spinal correction and fusion system, according to some embodiments.

FIG. 29 shows the system 10 employing a plurality of anchors, each of which is substantially similar to the first stabilizing anchor 16B (FIG. 26). As shown in FIG. 29, the rod 12 of the system 10 is able to slide and change in pitch, yaw and roll at the anchors 16B, 18B, 20B, 22B. The first anchor 16B optionally employs a chase feature similar to those previously described to limit roll. Alternatively, the first anchor 16B freely permits roll of the rod 12. As shown in FIG. 29, the rod 12 has a high degree of freedom, while being laterally constrained, as desired. In particular, the rod 12 is also able to be selectively locked against sliding, pitch, yaw, and roll at each of the anchors 16B, 18B, 20B, 22B as desired. Once again, selective locking at any of the anchors is optionally employed for a variety of reasons, including for performing partial or total fusion, to facilitate a correction, or adjustment process using the tensioners 32, 34, or to facilitate assembly of the system 10 prior to a correction operation. From the foregoing, it should be understood that a variety of numbers and configurations of the anchors is contemplated. Though not specifically shown, it should also be understood that any of the foregoing anchors are employed with the second rod 14 on the second side of the spine.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A system for correcting a spinal deformity, the system comprising:
   a first rod adapted to extend along a first side of a spine of a patient;
   a first anchor adapted to be fixed to a vertebra of the spine and to receive the first rod such that the first rod is secured against substantial lateral translation relative to the first anchor and the first rod is allowed to slide axially relative to the first anchor through a first pivot point and to change in at least two of pitch, yaw, and roll about the first pivot point during correction;
   a second anchor adapted to be fixed to a vertebra of the spine and to receive the first rod such that the first rod is secured against substantial lateral translation relative to the second anchor and is allowed to change in at least pitch and yaw about a second pivot point during correction;
   a second rod adapted to extend along a second side of the spine of the patient;
   a third anchor adapted to be fixed to a vertebra of the spine and to receive the second rod such that the second rod is secured against substantial lateral translation relative to the third anchor during correction and such that the second rod is secured against changes in pitch, yaw, roll, and axial sliding;
   a fourth anchor adapted to be fixed to a vertebra of the spine and to receive the second rod such that the second rod is secured against substantial lateral translation relative to the fourth anchor; and a lateral coupling adapted to extend between and laterally secure the first rod and the second rod such that the lateral coupling facilitates derotation and translation of the spine.

2. The system of claim 1, wherein the lateral coupling comprises:
an arm adapted to extend from the second side of the spine toward the first side of the spine and to receive the second rod,
a first flexible connector secured to the arm, and
an adjuster adapted to be secured to the first rod and to shorten an effective length of the first flexible connector to tension the arm toward the first rod.

3. The system of claim 2, wherein the arm is formed as a part of the third anchor.

4. The system of claim 2, wherein the third anchor includes a head defining a receptacle for receiving the second rod, a fixation member adapted to secure the head of the third anchor to the second side of the spine, and an arm extending from the head and adapted to extend from the second side of the spine to the first side of the spine.

5. The system of claim 4, wherein the third anchor includes a U-shaped receptacle for receiving the second rod.

6. The system of claim 4, wherein the fixation member includes a pedicle screw.

7. The system of claim 1, wherein the second rod is substantially shorter than the first rod.

8. The system of claim 1, wherein the second rod has a length corresponding to an apical region of a spine of a patient.

9. The system of claim 1, further comprising an anchor adapted to secure the first rod at a desired position and to secure the first rod against changes in pitch, yaw, roll, and axial sliding.

10. The system of claim 1, wherein the lateral coupling comprises:
an arm adapted to extend from the second side of the spine toward the first side of the spine and to receive the second rod,
a first connector secured to the arm, and
an adjuster adapted to tension the arm toward the first rod.

11. The system of claim 1, wherein the third anchor is adapted to secure the second rod at a desired position and to selectively secure the second rod against changes in pitch, yaw, roll, and axial sliding.

12. A system for correcting a spinal deformity, the system comprising:
a first rod adapted to extend along a first side of a spine of a patient;
a first anchor adapted to be fixed to a vertebra of the spine and to receive the first rod such that the first rod is secured against substantial lateral translation relative to the first anchor and the first rod is allowed to slide axially relative to the first anchor through a first pivot point and to change in at least two of pitch, yaw, and roll about the first pivot point during correction;
a second anchor adapted to be fixed to a vertebra of the spine and to receive the first rod such that the first rod is secured against substantial lateral translation relative to the second anchor and is allowed to change in at least pitch and yaw about a second pivot point during correction;
a second rod adapted to extend along a second side of the spine of the patient;
a third anchor adapted to be fixed to a vertebra of the spine and to receive the second rod such that the second rod is secured against substantial lateral translation relative to the third anchor;
a fourth anchor adapted to be fixed to a vertebra of the spine and to receive the second rod such that the second rod is secured against substantial lateral translation relative to the fourth anchor; and
a lateral coupling adapted to extend laterally between the first rod and the second rod such that the lateral coupling facilitates derotation and translation of the spine, the lateral coupling comprising:
an arm adapted to extend from the second side of the spine toward the first side of the spine and to receive the second rod;
an adjuster adapted to be secured to the first rod; and
a first connector adapted to be secured between the arm and the adjuster such that the adjuster is actuable to tension the arm toward the first rod.

13. The system of claim 12 configured such that actuation of the adjuster causes a first portion of the lateral coupling to engage with a second portion of the lateral coupling to generate a moment between the arm and the adjuster.

14. The system of claim 12 configured such that actuation of the adjuster causes a first portion of the lateral coupling to engage with a second portion of the lateral coupling to derotate and translate the spine.

15. The system of claim 12 configured such that actuation of the adjuster causes a first portion of the lateral coupling to engage with a second portion of the lateral coupling to adjust the distance between the first rod and the third anchor.

* * * * *